United States Patent [19]

Domagala et al.

[11] Patent Number: 5,668,162
[45] Date of Patent: Sep. 16, 1997

[54] ISOTHIAZOLONES LOWER PLASMA LEVELS OF LIPOPROTEIN(A)

[76] Inventors: John Michael Domagala, 47693 Red Run, Canton, Mich. 48187; Helen Tsenwhei Lee, 3625 Fox Hunt; Randy Ranjee Ramharack, 2465 Antietam Dr., both of Ann Arbor, Mich. 48105; Bruce David Roth, 6089 White Swan La.; Tomi Sawyer, 5753 E. Silo Ridge, both of Ann Arbor, Mich. 48108; Drago Robert Sliskovic, 3679 Hedgerow Dr., Saline, Mich. 48176

[21] Appl. No.: 646,188

[22] Filed: May 7, 1996

Related U.S. Application Data

[63] Continuation-in-part of Ser. No. 456,149, May 31, 1995.

[51] Int. Cl.$^6$ .................................................. A61K 31/41
[52] U.S. Cl. .................... 514/373; 514/258; 514/301
[58] Field of Search ................................ 514/373, 258, 514/301; 548/209

[56] References Cited

U.S. PATENT DOCUMENTS

| | | | |
|---|---|---|---|
| 3,012,039 | 12/1961 | Morley et al. | 260/304 |
| 3,517,022 | 6/1970 | Miller et al. | 260/304 |
| 3,661,974 | 5/1972 | Grivas | 260/470 |
| 3,761,489 | 9/1973 | Grivas | 260/304 |
| 3,965,107 | 6/1976 | Rainey et al. | 260/294.8 |
| 4,049,817 | 9/1977 | Laber et al. | 424/270 |
| 4,093,730 | 6/1978 | Butti et al. | 424/270 |
| 4,156,729 | 5/1979 | Böshagen et al. | 424/270 |
| 4,458,942 | 7/1984 | Shroot et al. | 514/301 |
| 4,512,985 | 4/1985 | Maignan et al. | 514/301 |
| 5,153,212 | 10/1992 | Shroot et al. | 514/372 |
| 5,219,875 | 6/1993 | Sherba et al. | 514/373 |

FOREIGN PATENT DOCUMENTS

| | | |
|---|---|---|
| 0633260 | 1/1995 | European Pat. Off. |
| 861326 | 5/1978 | France . |
| 477476 | 3/1992 | Japan . |
| 1306493 | 2/1973 | United Kingdom . |
| 1560726 | 2/1980 | United Kingdom . |

OTHER PUBLICATIONS

Okachi, et al., *J. Med. Chem.*, vol. 28, No. 12, pp. 1772–1779 (1985).

Carmellino, et al., *Eur. J. Med. Chem.*, vol. 29, pp. 743–751 (1994).

Schaper, *Synthesis*, pp. 861–867 (1985).

Auerbach, et al., *Analytical Biochemistry*, vol. 201, pp. 375–380 (1992).

*Primary Examiner*—Robert Gerstl
*Attorney, Agent, or Firm*—Charles W. Ashbrook

[57] ABSTRACT

Plasma levels of Lp(a) are lowered by administering an isothiazolone having the general structure

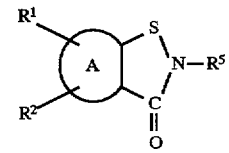

where A is a monocyclic or bicyclic ring which may contain up to 3 heteroatoms selected from O, S, and N; $R^1$ and $R^2$ are substituent groups such as alkyl, alkoxy, hydroxy, nitro, cyano, amino, and carboxy; and $R^5$ is alkyl, cycloalkyl, phenyl, and Het.

17 Claims, No Drawings

ISOTHIAZOLONES LOWER PLASMA LEVELS OF LIPOPROTEIN(A)

This is a continuation-in-part of U.S. application Ser. No. 08/456,149 filed May 31, 1995 allowed.

FIELD OF THE INVENTION

This invention relates to a method for lowering plasma levels of a lipoprotein known as lipoprotein(a), Lp(a), in animals comprising administering an isothiazolone.

BACKGROUND OF THE INVENTION

Heart disease remains one of the leading causes of death. The high incidence of heart disease has led to the identification of various risk factors that may be controlled in an effort to reduce such disease. One risk factor is hypercholesterolemia, which is a condition of high blood levels of cholesterol. Cholesterol is a fatty substance that is made by the liver, and also is present in many foods. Cholesterol circulates in the blood associated with several forms of lipoproteins. Some of these forms are now referred to as "good" forms of cholesterol, while others are "bad". For example, one such lipoprotein with which cholesterol associates is referred to as low-density lipoprotein or LDL. LDL-cholesterol (LCL-C) is the form in which cholesterol leaves the liver destined for cells throughout the body. High levels of LDL-C are bad, because they have been shown to cause rapid clogging of coronary arteries with fatty deposits, resulting in the disease known as atherosclerosis, which often leads to heart attacks. A great deal of effort is currently underway to get people to reduce their levels of LDL-C, for example, by modifying diet and exercise.

In contrast, a good form of cholesterol is that associated with high-density lipoprotein, i.e., HDL-cholesterol (HDL-C). This is the form in which cholesterol is pulled out of cells and goes back to the liver for disposal.

A modified form of LDL is known as lipoprotein(a), "Lp(a)". It consists of LDL covalently linked through a disulfide bond to apolipoprotein(a), "apo(a)" Lp(a) cholesterol appears to be a bad form of cholesterol, since elevated levels of Lp(a) have been associated with the development of a variety of vascular diseases including atherosclerosis, coronary heart disease, angina, myocardial infarction, cerebral infarction, ischemic stroke, and restenosis following balloon angioplasty. In fact, Lp(a) appears to be an excellent predictor for stroke. Accordingly, high concentrations of Lp(a) is one of the major risk factors leading to death from heart disease.

We have now discovered that isothiazolones are effective in lowering plasma concentrations of Lp(a). This invention thus provides a method for lowering plasma levels of Lp(a) comprising administering a isothiazolone.

Certain isothiazolones are known which have various pharmaceutical utilities, most notably antimicrobial activity. Okachi, et al., *J. Med. Chem.*, 1985;28:1772–1779, describe several 1,2-benzisothiazolones which have marginal antibiotic activity and which were primarily utilized as intermediates in the synthesis of 2,2'-dithiobis (benzamide) derivatives. Carmellino, et al., *Eur. J. Med. Chem.*, 1994;29:743–751, disclose a variety of 1,2-benzisothiazolones as antibacterial and antifungal agents. Miller, et al., U.S. Pat. No. 3,517,022, disclose 2-carbamoyl-1, 2-benzisothiazolones which are said to be active against bacteria, fungi, and algae. Morley, in U.S. Pat. No. 3,012,039, describes 2-alkyl-1,2-benzisothiazolones which are useful as antibacterials and antifungals. Sherba, et al., U.S. Pat. 5,219,875, describe synergistic antimicrobial compositions 5 comprising 2-unsubstituted 1,2-benziso-thiazolin-3-one and iodopropargyl butylcarbamate. Laber, et al., U.S. Pat. No. 4,049,817, describe synergistic antimicrobial compositions containing a variety of 2-substituted and 2-unsubstituted benzisothiazolinones.

Grivos, U.S. Pat. No. 3,761,489, describes a series of substituted N-alkyl benzisothiazolinones which are said to be active against bacteria, fungi, and yeasts. Grivos, U.S. Pat. No. 3,661,974, describes the synthesis of various 2-substituted 1,2-benzisothiazolin-3-ones from 2-carbalkoxy-phenyl sulfonamides. The thiazolinones are said to be useful as antibacterials and antiseptics.

There have been no reports that isothiazolones effect plasma levels of Lp(a). We have now discovered that plasma Lp(a) can be lowered by administering an isothiazolone, and accordingly an object of this invention is to provide a method for lowering Lp(a), and thereby treating and preventing coronary artery disease.

SUMMARY OF THE INVENTION

This invention provides a method for lowering plasma levels of Lp(a) using an isothiazolone. More particularly, the invention is a method for lowering plasma levels of Lp(a) in animals comprising administering to an animal an Lp(a) lowering amount of an isothiazolone of Formula I.

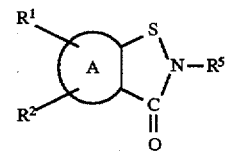

wherein:

A is a monocyclic ring having 5 or 6 ring atoms, or a bicyclic ring having from 9 to 12 ring atoms, the ring atoms being selected from carbon and optionally up to 3 heteroatoms selected from O, S, and N.

$R^1$ and $R^2$ independently are hydrogen, halo, $C_1$-$C_6$ alkyl, $C_3$-$C_6$ cycloalkyl, Het$(CR^6R^7)_m$-, phenyl-$(CR^6R^7)_m$-, O-$C_1$-$C_6$ alkyl, hydroxy, nitro, cyano, $NR^3R^4$, $NR^3COR^4$, $CO_2R^3$, $CONR^3R^4$, $S(O)_mR^3$, $SO_3H$, $S(O)_mNR^3R^4$, $COR^3$, or taken together are oxo (O=) or methylene dioxy (-O-$CH_2$-O-);

m is 0, 1, or 2;

$R^3$ and $R^4$ independently are hydrogen, $C_1$-$C_6$ alkyl, $C_3$-$C_6$ cycloalkyl, Het$(CR^6R^7)_m$-, or phenyl-$(CR^6R^7)_m$-;

$R^6$ and $R^7$ independently are hydrogen, $C_1$-$C_6$ alkyl, $CO_2R^3$, hydroxy, $CONR^3R^4$, or cyano;

$R^5$ is hydrogen, $C_1$-$C_6$ alkyl, $COC_1$-$C_6$ alkyl, $C_3$-$C_6$ cycloalkyl, phenyl-$(CR^6R^7)_m$-, Het$(CR^6R^7)_m$-; and wherein the foregoing alkyl, cycloalkyl, phenyl, and Het groups may optionally be substituted with from 1 to 3 groups selected from halo, hydroxy, nitro, $NR^3R^4$, $NR^3COR^4$, $CO_2R^3$, $CONR^3R^4$, $S(O)_mR^3$, $S(O)_mNR^3R^4$, and $COR^3$, where m, $R^3$, and $R^4$ are as defined above;

and the pharmaceutically acceptable salts and solvates thereof.

In a preferred embodiment, the isothiazolones utilized in the methods of this invention have Formula I above wherein A is a monocyclic ring having 6-ring atoms, one or two of which are heteroatoms selected from O, S, and N; ideally N.

In a further preferred embodiment, A is a monocyclic aromatic ring having 6-ring atoms, one or two of which are O, S, or N; ideally N. Especially preferred compounds within this group have the formulas

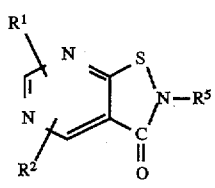

and

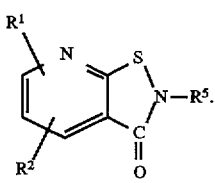

In another preferred embodiment, the isothiazolones utilized in the methods of the invention are benzisothiazolin-3-ones of Formula II

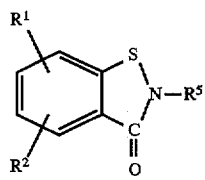

where $R^1$ and $R^2$ independently are hydrogen, halo, $C_1$-$C_6$ alkyl or O-$C_1$-$C_6$ alkyl, and $R^5$ is $C_1$-$C_6$ alkyl, substituted $C_1$-$C_6$ alkyl, or unsubstituted or substituted phenyl-$(CR^6R^7)_m$-.

An especially preferred method for lowering Lp(a) employs a compound having the Formula III

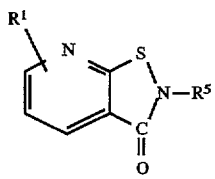

where $R^1$ is hydrogen, halo, alkyl or alkoxy, and $R^5$ is $C_1$-$C_6$ alkyl substituted with 1 or 2 CO $R^3$ groups, or phenyl substituted with $S(O)_m NR^3R^4$, where $R^3$ and $R^4$ are as defined above.

Another preferred method for lowering Lp(a) employs a compound of Formula IIa and Formula IVb

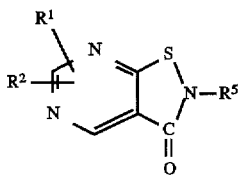

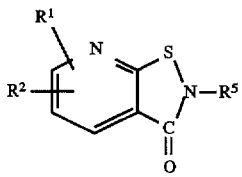

where $R^1$, $R^2$, and $R^5$ are as defined above. By lowering Lp(a) levels, the animals are protected against developing premature atherosclerosis and consequent coronary artery disease.

DETAILED DESCRIPTION OF THE INVENTION

"$C_1$-$C_6$ alkyl" means a straight or branched aliphatic group having from 1 to 6 carbon atoms. Examples include methyl, ethyl, isobutyl, n-pentyl, and isohexyl.

The term "O-$C_1$-$C_6$ alkyl" means the foregoing alkyl radicals bonded through oxygen, examples of which include methoxy, ethoxy, isopropoxy, tert-butoxy, and the like. Typical "$C_3$-$C_6$ cycloalkyl" groups include cyclopropyl, cyclopentyl, cyclohexyl, and the like.

"Het" is a cyclic or bicyclic ring having from 4 to 10 atoms, from one to four of which are selected from O, S, or N. Het includes non-aromatic groups such as morpholino and pyrrlidino. Preferred Het groups are 5- or 6-membered mono-cyclic aromatic rings having 1 or 2 heteroatoms. Het includes bicyclic rings such as benzofuran, isothiazolone, indole, and the like. Typical groups represented by Het include

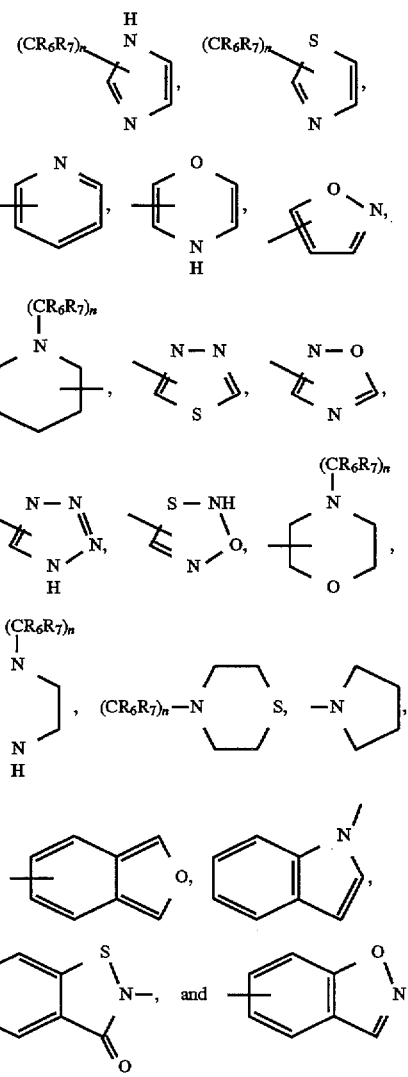

and the like. Other typically preferred Het groups include pyrimidine, pyridazine, pyrazine, oxazole, pyrazole, thiazole, and the like.

As noted above, the alkyl, cycloalkyl, phenyl and Het groups which are included in the definitions of $R^1$, $R^2$, $R^3$, $R^4$, and $R^5$ can be substituted with 1 to 3 groups selected from halo, hydroxy, $NR^3COR^4$, $CO_2R^3$, $NR^3R^4$, $CONR^3R^4$, $S(O)_mR^3$, $SO_3H$, $S(O)_mNR^3R^4$, and $COR^3$, where m, $R^3$, and $R^4$ are as defined above. Typical substituted alkyl groups thus include chloromethyl, 3-bromopropyl, trifluoromethyl, 4-hydroxyhexyl, 1-carboxy-2-methylbutyl, 3-methylthiobutyl, 4-methylsulfonylbutyl, dimethylaminomethyl, 2,3-dibromobutyl, 2-amino-3-chloro-4-carboxybutyl, 3-acetomidopropyl, 2-acetylethyl, 2-methoxycarbonylethyl, 1,1-diacetylpropyl, and the like.

Preferred substituted alkyl groups are those having 1, 2, or 3 substituents selected from halo, hydroxy, and carboxy. Such preferred groups include 1-bromo-2-hydroxypropyl, 1,1-dimethyl-3-hydroxypropyl, 1-hydroxymethyl-2-fluoromethyl-3-carboxybutyl, 1-carboxy-2-methylbutyl, 1-carboxy-3-methylbutyl, 1,2,3-trihydroxypentyl, and the like.

Typical substituted cycloalkyl groups include 2-fluorocyclopropyl, 2,2-dibromocyclopropyl, 2-carboxycyclobutyl, 2-aminosulfonylcyclopentyl, 2-amino-3-carboxycyclopentyl, and 3-isopropylsulfinylcyclohexyl.

In the above formulas, $R^1$ and $R^2$ can be halo, which term includes fluoro, chloro, bromo, and iodo. $R^1$, $R^2$, and $R^5$ can include the group phenyl-$(CR^6R^7)_m$- in which the phenyl can be unsubstituted or substituted with halo, hydroxy, $NR^3R^4$, $NR^3COR^4$, $CO_2R^3$, $CONR^3R^4$, $S(O)_mR^3$, $S(O)_mNR^3R^4$, $SO_3H$, and $COR^3$. Typical $NR^3R^4$ substituents include amino, methylamino, dimethylamino, ethylisohexylamino, cyclopropylamino, 3-pyridylamino, N-methyl-2-thienylamino, benzylamino, and 3-chlorobenzylamino.

Typical substituents defined by $NR^3COR^4$ include cyclopropylcarbonylamino, N-isobutyl-N-cyclohexyl carbonylamino, acetamido, and the like. Typical groups defined by $CO_2R^3$ include the free carboxy acid when $R^3$ is hydrogen, and esters such as $C_1$-$C_6$ alkyl esters, benzyl esters, cyclobutyl esters, and the like. Amide substituents are defined by $CONR^3R^4$, and include carboxamide, N-methyl-carboxamide, and N,N-diethyl-carboxamide. Typical $S(O)_m R^3$ substituent groups include methylthio, ethylsulfinyl, cyclopropylsulfonyl, and the like. Sulfonamide substituents $S(O)_mNR^3R^4$ include N-methylsulfonamide, N,N-dimethylsulfonamide, and the like. Typical phenyl-$(CR^6R^7)_m$- groups substituted with the foregoing substituent groups thus include:

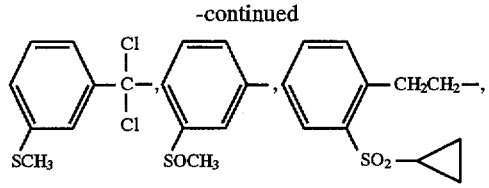

-continued

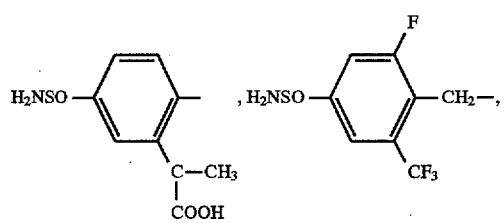

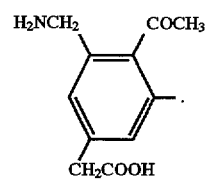

and

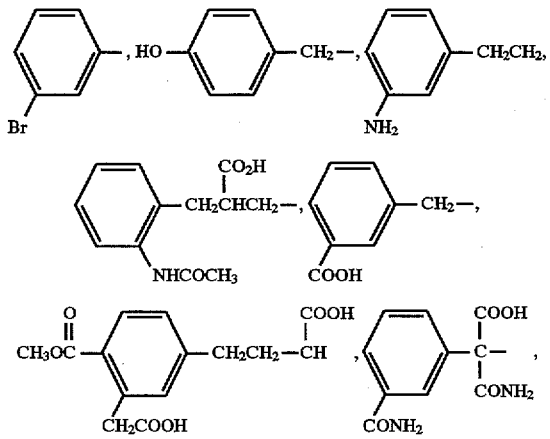

The compounds of the invention can be bicyclic or tricyclic, for example, when A in Formula I is a monocyclic ring or a bicyclic ring, respectively. The compounds can have from 1 to 3 heteroatoms selected from O, S, and N as part of the A ring system. Typical bicyclic and tricyclic isothiazolones contemplated herein include:

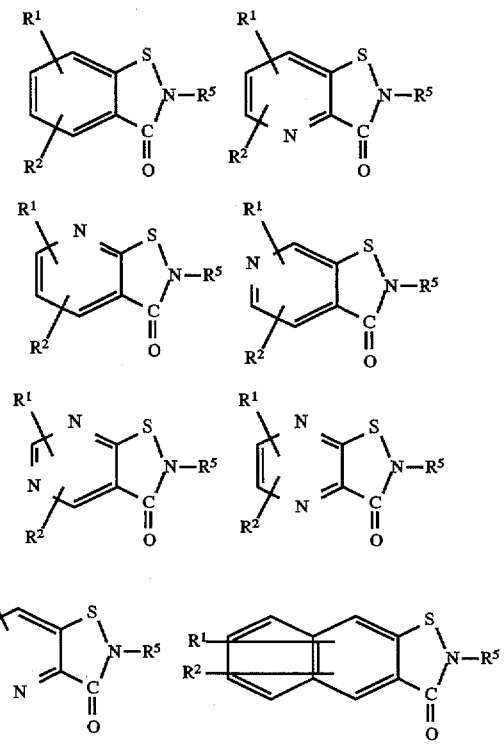

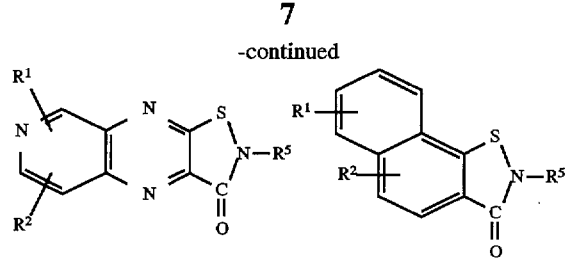
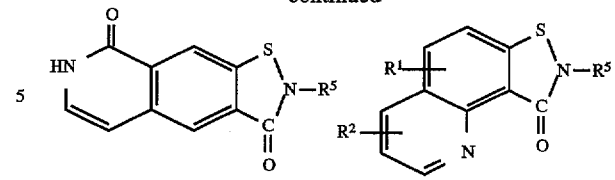

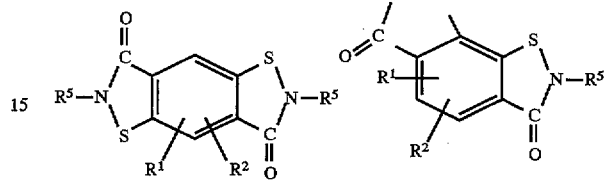

Typical substituted $Het(CR^6R^7)_m$- include:

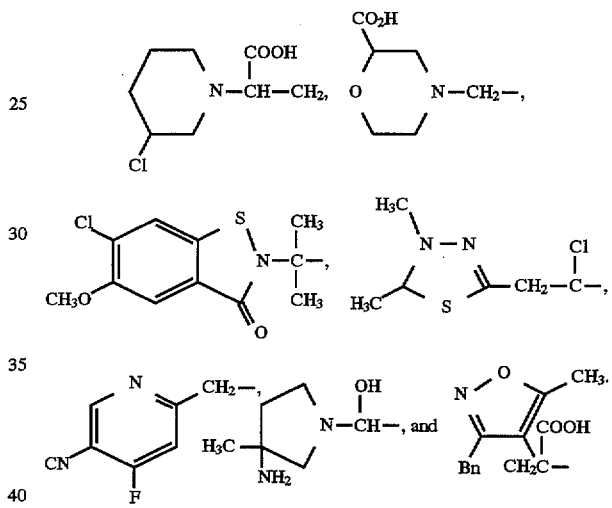

The compounds to be utilized to lower Lp(a) according to this invention can be prepared by any of several synthetic processes utilizing common methodology. For example, an O-halosulfenylbenzoyl halide can be reacted with an amine according to the following scheme, which is the general method of Fisher and Hurni, *Arzneithmittel Forsch.*, 1964;14:1301:

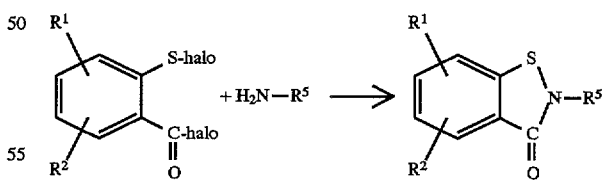

where $R^1$, $R^2$, and $R^5$ are as defined above, and "halo" includes chloro, bromo, iodo, and the like. Typically, the amine and halosulfenylbenzoyl halide are employed in approximately equimolar quantities; however, an excess of the amine can be utilized if desired. The reaction generally is substantially complete within about 1 to 8 hours when carried out in a mutual solvent such as toluene, ethylene dichloride, or methylene chloride at a temperature of about 0° C. to 45° C. Acid scavengers, such as triethylamine, can be utilized if desired. The product isothiazolone is readily isolated by removing the reaction solvent, and further purification can be accomplished by crystallization or chromatography, if desired. The process is equally applicable to all A systems contemplated.

An alternative method of synthesis comprises reacting a 2-unsubstituted isothiazolone with a compound $R_5L$, where L is a leaving group such as halo. This reaction is depicted as follows:

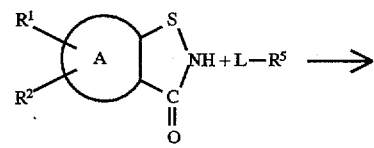

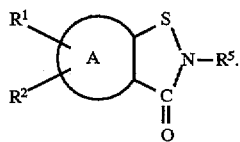

Specific reaction conditions, such as choice of solvents, temperature, molar ratios, acid scavengers, and the like, are similar to the process described above, and are well within the skill of the art.

A preferred method for preparing the isothiazolones comprises disproportionation of a 2,2'-dithiobisaryl amide by reaction with an oxidizing agent such as chlorine or bromine according to the following scheme:

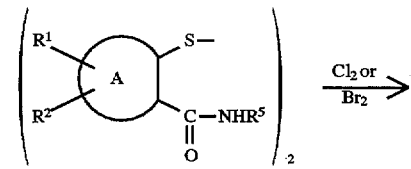

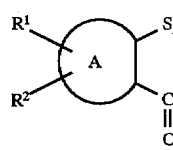

where $R^1$, $R^2$, and $R^5$ are as defined above. This disproportionation reaction requires starting with a 2,2'-dithiobisaryl amide, and these are readily prepared from 2,2'-dithiobisaryl carboxylic acids by reacting the acid with a chlorinating agent such as oxalyl chloride or thionyl chloride to produce the corresponding acid chloride, and then reacting the acid chloride with an amine $R_5NH_2$. A typical synthesis follows the following scheme:

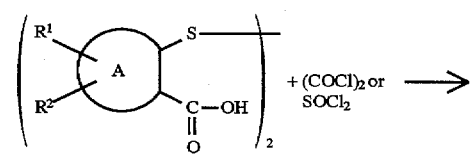

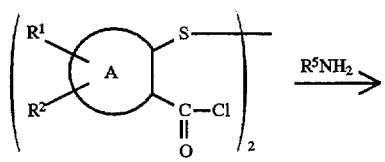

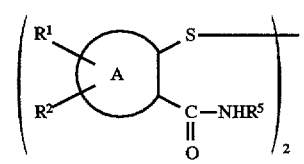

The 2,2'-dithiobisaryl carboxylic acids required for the above synthesis are well known in the art or are readily prepared by routine methods. Typical aryl carboxylic acids commonly used include those of the following general structures:

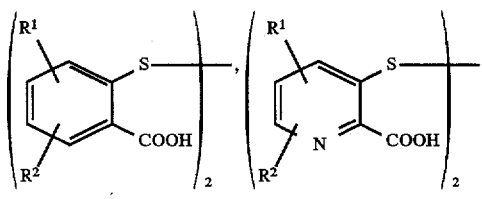

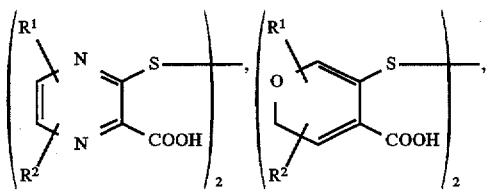

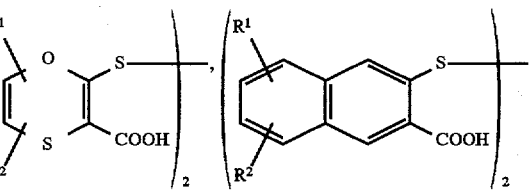

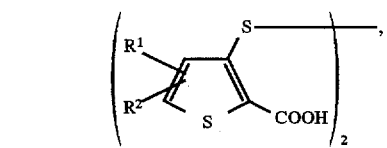

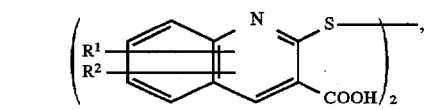

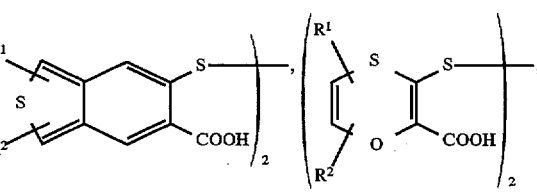

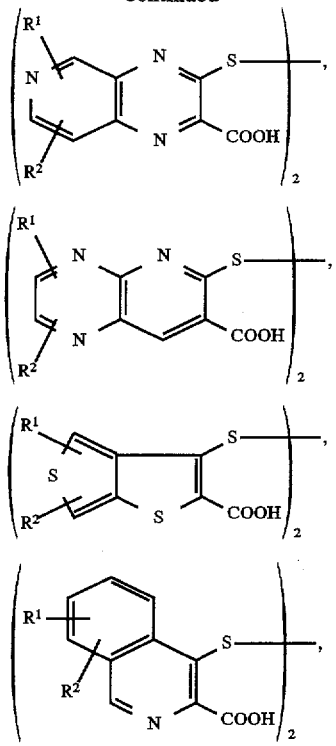

The 2,2'-dithiobisaryl carboxylic acids are readily converted to the corresponding acid chlorides by reaction with a chlorinating agent such as thionyl chloride or oxalyl chloride. The reaction can be carried out neat or in an unreactive organic solvent such as dichloromethane, tetrahydrofuran, diethyl ether, dimethylformamide, or the like. The reaction generally is complete within about 1 to about 8 hours when carried out at a temperature of about 0° C. to about 100° C. The product acid chlorides are readily isolated simply by removing the reaction solvent and excess chlorinating agent, for example by evaporation under reduced pressure.

The 2,2'-dithiobisaryl carboxylic acid chlorides are next converted to 2,2'-dithiobisarylamides by reaction with a primary amine of the formula $R^5NH_2$. Typical primary amines commonly employed include alkyl amines and substituted alkyl amines such as methylamine, leucine, isoleucine, serine, threonine, lysine, asparagine, and the like. Aniline and substituted anilines can also be employed, such as 4-hydroxyaniline, 3-aminoaniline, 3-methylthioaniline, 4-dimethylsulfamoylaniline, and the like. The amine and acid chloride generally are mixed in approximately equimolar quantities in a mutual solvent such as acetone, dichloromethane, tetrahydrofuran, methanol, and the like. Acid scavengers such as pyridine, triethylamine, N-methylmorpholine, and the like, can be utilized if desired. The reaction generally is complete within about 1 to about 18 hours when carried out at a temperature of about 0° C. to about 100° C. The 2,2'-dithiobisaryl amides that are formed are easily isolated by simply removing the reaction solvents and any excess reactants by evaporation under reduced pressure, and further purification generally is not required.

The 2,2'-dithiobisaryl carboxamides can be converted to the isothiazolones of the invention in either of two ways. The carboxamides readily react with oxidizing agents such as bromine or chlorine to effect cyclization to the corresponding isothiazolones. The oxidation generally is carried out by mixing an excess of chlorine or bromine with the carboxamide in a suitable solvent such as a halogenated hydrocarbon, dimethylsulfoxide, dimethylformamide, or the like, typically at a reduced temperature of about 0° C. to about 5° C. The product isothiazolone is generally solid at room temperature and normally precipitates from the reaction mixture. It can be recovered by filtration, and further purified, if desired, by routine methods such as washing, for instance with aqueous sodium bicarbonate or the like, and crystallized from common solvents such as acetone, ethanol, ethyl acetate, and the like.

An alternative method for making the isothiazolones from the 2,2'-dithiobisaryl carboxamides comprises first converting the dithiobis intermediate to the corresponding aryl thiol carboxamide derivative, and then cyclizing the thiol and carboxamide to form the final product. This scheme is depicted below:

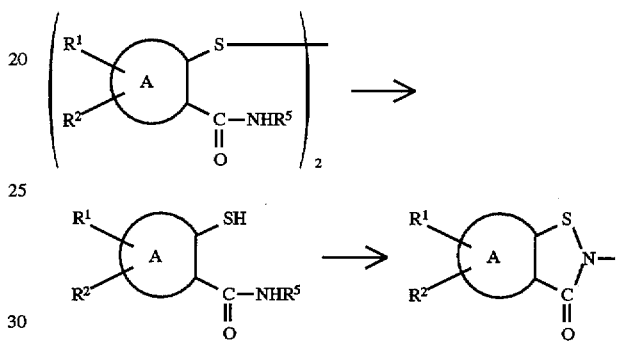

The dithiobis intermediates are reacted with a reducing agent such as dithiothreitol (DTT) in a mutual solvent such as dimethylformamide, dimethylsulfoxide, dioxane, and the like. The reduction typically is carried out at a temperature of about 10° C. to about 30° C., and normally is complete within about 0.5 to about 4 hours. The product aryl thiol carboxamide generally is not isolated, other than removing any reaction solvent by evaporation.

The aryl thiol carboxamide can also be prepared from readily available 2-hydroxycarboxylic acids according to the following scheme:

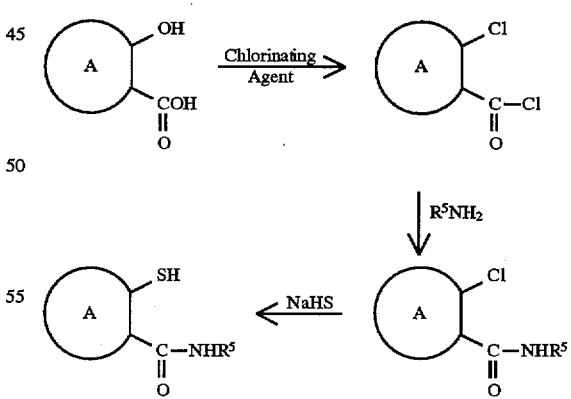

In this process, a 2-hydroxycarboxylic acid is reacted with an excess of a common chlorinating agent such as thionyl chloride or phosphorus pentachloride in an unreactive organic solvent such as ethylene dichloride, chloroform, ethyl chloride, toluene, or the like, typically at a temperature of about 25° C. to about 60° C. The product, a 2-chloro acid chloride derivative, generally is isolated by simply removing the reaction solvent and excess chlorinating agent, for instance by evaporation under reduced pressure. The chloro acid chloride is then reacted with a primary amine, $R^5NH_2$, in an unreactive organic solvent such as chloroform, methylene chloride, ethyl chloride, or the like. Typical primary amines commonly employed include natural α-amino acids such as glycine, leucine, isoleucine, lysine, aspartic acid, and the like. Tertiary and aromatic amines such as triethylamine, pyridine, or N-methyl morpholine can be added to act as acid scavenger for the hydrochloric acid that is formed during the reaction. The chloro carboxamide that is produced is readily isolated by removing the reaction solvent, and further purification can be accomplished by routine methods such as crystallization, chromatography, and the like. The chloro carboxamide is next reacted with sodium hydrogen sulfide in a polar solvent such as methanol, ethanol, isopropanol, or the like to give the corresponding 2-thiol carboxamide derivative.

The aryl thiol carboxamide is next reacted with an agent to effect cyclization. Typical agents routinely utilized include chlorocarbonyl sulfenyl chloride, iodine, bromine, and the like. The cyclization is accomplished by mixing equimolar quantities of the thiol carboxamide and cyclizing agent in an unreactive organic solvent such as tetrahydrofuran or the like, and stirring the mixture for about 0.5 to about 18 hours at a temperature of about 0° C. to about 30° C. The product isothiozolone typically precipitates as it is formed, and is readily isolated by filtration, and further purified, if desired, by crystallization, chromatography, and the like.

Many of the compounds embraced by Formula I can have functional substituent groups (e.g., $R^1$ and $R^2$) which may need to be derivatized in order to avoid unwanted side reactions during synthesis. Such functional substituent groups include, for example, hydroxy groups, amino groups, especially primary and secondary amino groups, and carboxylic acid groups. For example, hydroxy groups, in order to prevent unwanted side reactions, generally need to be converted to protected hydroxy groups such as ethers or esters during chemical reactions at other sites in the molecule. The hydroxy protecting group is subsequently removed to provide the free hydroxy group. Amino groups and carboxylic acid groups are similarly derivatized to protect them against unwanted side reactions. Carboxy groups generally are converted to esters such as tert-butyl ester, benzyl or p-nitrobenzyl ester, and the like. Amino groups typically are acylated, for example with acetyl 5 chloride or the like, or silylated with trimethylsilyl or t-butyldimethylsilyl groups. Typical protecting groups, and methods for attaching and cleaving them, are described fully by Greene and Wuts in *Protective Groups in Organic Synthesis,* John Wiley and Sons, New York, (2nd Ed; 1991), and McOmie, *Protective Groups in Organic Chemistry,* Plenum Press, New York, 1973.

Many of the isothiazolones of Formula I are capable of forming pharmaceutically acceptable salts, including acid addition salts and base salts, as well as solvates, such as hydrates and alcoholates. All of these pharmaceutical forms are contemplated by this invention and are included herein. Acid addition salts are readily formed when a Formula I compound contains amino substituent groups, or nitrogen atoms are present in the A ring system. Base salts can be formed when carboxylic acid substituent groups are present, for example, when $R^5$ is a carboxy substituted alkyl such as carboxymethyl or the like.

Pharmaceutically acceptable acid addition salts of the compounds of Formula I include salts derived from inorganic acids such as hydrochloric, nitric, phosphoric, sulfuric, hydrobromic, hydriodic, phosphoric, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, factate, maleate, tartrate, methanesulfonate, and the like. Also contemplated are salts of amino acids such as arginate and the like and gluconate, galacturonate (see, for example, Berge S. M., et al., "Pharmaceutical Salts," *J. of Pharmaceutical Science,* 1977;66:1–19).

The acid addition salts of basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge S. M., et al., "Pharmaceutical Salts," *J. of Pharmaceutical Science,* 1977;66:1–19).

The base addition salts of acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Many of the isothiazolones of Formula I contain one or more asymmetric carbon atoms, and as such, can exist in optically active forms. For example, a preferred group of compounds are those wherein $R^5$ is a residue of an α-amino acid such as alanine, valine, leucine, threonine, and the like. Such groups have one or more asymmetric centers. The racemates can be separated into their respective enantiomers by routine methodology, including fractional crystallization, high performance liquid chromatograph, asymmetric synthesis, and the like. The racemates and individual enantiomers are contemplated equally by this invention.

While the forms of the invention herein constitute presently preferred embodiments, many others are possible. It is not intended herein to mention all of the possible equivalent forms or ramifications of the invention. It is understood that the terms used herein are merely descriptive rather than limiting, and that various changes may be made without departing from the spirit or scope of the invention.

The following detailed examples illustrate specific embodiments of the invention. The examples are intended to be a general illustration of how to make and use the invention, and are not intended to be limiting in any respect.

Unless otherwise stated, all reagents were obtained from commercial sources. Many of the aryl thiol carboxamides which are utilized as starting materials are known or are available by the methods described, for example, by Bell, *J. Am. Chem. Soc.,* 1942:2905, Carmellino, et al., *Eur. J. Med. Chem.,* 1994;29:743–751, Bennett, et al., *Organic Prep. and Proced. Int.,* 1974;6(6):287–293 and Vitali, et al., Il Farmaco Ed. Sc., 1968;23:468–476. These references are incorporated herein by reference for their teaching of synthetic methods for aryl thio carboxamides.

PREPARATION 1

2,2'-Dithiobisbenzoyl chloride

A mixture of 2,2'-dithiobisbenzoic acid (25 g, 81.6 mmol) in 350 mL of thionyl chloride was heated at reflux for 18 hours. The resulting solution was cooled and excess thionyl chloride was removed in vacuo. The crude solid was slurried in hexane and the title compound was recovered by filtration to yield 21.2 g, mp 150°–151° C. This compound was used without further purification.

PREPARATION 2

2,2'-Dithiobis[5-fluorobenzoyl chloride]

A mixture of 2,2'-dithiobis[5-fluorobenzoic acid] (5.0 g, 14.6 mmol) and thionyl chloride (40 mL) was reacted according to the procedure described above to yield 4.9 g of 2,2'-dithiobis[5-fluorobenzoyl chloride]. This compound was used without further purification.

PREPARATION 3

2,2'-Dithiobis[5-methoxybenzoyl chloride]

A mixture of 2,2'-dithiobis[5-methoxybenzoic acid] (0.8 g, 2.0 mmol) and thionyl chloride (10 mL) was reacted according to the procedure described above to yield 0.8 g of 2,2'-dithiobis[5-methoxybenzoyl chloride]. This compound was used without further purification.

PREPARATION 4

2,2'-Dithiobis[5-methylbenzoic acid]

A mixture of 2,2'-dithiobis[5-methylbenzoic acid] (0.6 g, 1.8 mmol) and thionyl chloride (10 mL) was reacted according to the procedure described above to yield 0.3 g of 2,2'-dithiobis[5-methylbenzoyl chloride]. The compound was used without further purification.

PREPARATION 5

2,2'-Dithiobis[4-fluorobenzoyl chloride]

A mixture of 2,2'-dithiobis[4-fluorobenzoic acid] (5.0 g, 14.6 mmol) and thionyl chloride was reacted according to the procedure described above to yield 4.1 g of 2,2'-dithiobis[4-fluorobenzoyl chloride]. The compound was used without further purification.

PREPARATION 6

2,2'-Dithiobis[4-methoxybenzoyl chloride]

A mixture of 2,2'-dithiobis[4-methoxybenzoic acid] (2.2 g, 6.6 mmol) and thionyl chloride (20 mL) was reacted according to the procedure described above to yield 2.1 g of 2,2'-dithiobis[4-methoxybenzoyl chloride]. No further purification was required.

PREPARATION 7

2,2'-Dithiobis[4-methylbenzoyl chloride]

A mixture of 2,2'-dithiobis[4-methylbenzoic acid] (3.8 g, 11.9 mmol) and thionyl chloride (50 mL) was reacted according to the procedure described above to yield 3.6 g of 2,2'-dithiobis[4-methylbenzoyl chloride]. The compound was used without further purification.

PREPARATION 8

2,2'-Dithiobis[3-pyridinecarbonyl chloride]

A mixture of 2,2'dithiobis[3-pyridinecarboxylic acid] (1.5 g, 4.8 mmol) and thionyl chloride (20 mL) was reacted according to the procedure described above to yield 1.3 g of 2,2'-dithiobis[3-pyridinecarbonyl chloride]. The compound was used without further purification.

PREPARATION 9

2,2'-Dithiobis[4'-sulfamoylbenzanilide] (general method)

A solution of 2,2'-dithiobisbenzoyl chloride (5.0 g, 14.0 mmol) from Preparation 1 in 50 mL of dichloromethane was added dropwise to a solution of 4-(aminosulfonyl)-aniline (6.2 g, 36.0 mmol) in 125 mL pyridine cooled to 0° C. The mixture was stirred for 18 hours, and the resulting solid was removed by filtration, washed with 1N HCl, water, and dried in vacuo to yield 7.6 g of crude product. This crude material (6.5 g) was suspended in 50 mL dimethylformamide/60 mL ethanol, filtered, and precipitated from the filtered solution with the addition of 10 mL 4% aqueous $NaHCO_3$. The product was collected by filtration, washed with ethanol and water to yield 4.3 g of the title compound, mp 311°–312° C.

PREPARATION 10

2,2'-Dithiobis[4'-sulfamoyl(4-methoxybenzanilide)]

This compound was prepared according to the general method described in Preparation 9 using 2,2'-dithiobis[4-methoxybenzoyl chloride] (1.1 g, 2.7 mmol) in dichloromethane (10 mL) and 4-(aminosulfonyl)-aniline (1.1 g, 6.8 mmol) in pyridine (15 mL). The crude product was recrystallized from dimethylformamide, ethanol, and water to yield 0.8 g of the title compound.

PREPARATION 11

2,2'-Dithiobis[4'-sulfamoyl(4-methylbenzanilide)]

This compound was prepared according to the general procedure described in Preparation 9 using 2,2'-dithiobis[4-methylbenzoyl chloride] (2.0 g, 5.5 mmol) in dichloromethane (20 mL) and 4-(aminosulfonyl)-aniline (3.4 g, 19.9 mmol) in pyridine (40 mL). The crude product was recrystallized from dimethylformamide, ethanol, and water to afford 2.1 g of the title compound.

PREPARATION 12

2,2'-Dithiobis[4'-sulfamoyl(4-fluorobenzanilide)]

This compound was prepared according to the general procedure described in Preparation 9 using 2,2'-dithiobis[4- fluorobenzoyl chloride] (2.0 g, 5.2 mmol) in dichloromethane (20 mL) and 4-(aminosulfonyl)-aniline (2.2 g, 13.0 mmol) in pyridine (30 mL). The crude product was recrystallized from dimethylformamide, ethanol, and water to yield 2.6 g of the title compound.

PREPARATION 13

2,2'-Dithiobis[4'-sulfamoyl(5-methylbenzanilide)]

This compound was prepared according to the general method of Preparation 9 using 2,2'-dithiobis[5-methylbenzoyl chloride] (2.0 g, 5.3 mmol) in dichloromethane (20 mL) and 4-(aminosulfonyl)-aniline (2.3 g, 13.3 mmol) in pyridine (30 mL). The crude product was recrystallized from dimethylformamide, ethanol, and water to yield 1.8 g of the title compound.

PREPARATION 14

[S-(R*,R*)]-2-[2-[2-(1-tert-Butoxycarbonyl-3-methyl-butylcarbamoyl)-5-methoxy-phenyldisulfanyl]-4-methoxy-benzoylamino]-4-methyl-pentanoic acid tert-butyl ester (general method)

A solution of 2,2'-dithiobis[4-methoxybenzoyl chloride] (1.1 g, 2.7 mmol) from Preparation 9 in 10 mL of dichloromethane was added dropwise to a solution of L-leucine, t-butyl ester, monohydrochloride (1.5 g, 6.8 mmol) and N-methyl morpholine (1.6 mL, 14.0 mmol) in 25 mL dichloromethane cooled to 0° C. to 5° C. The resulting solution was stirred for 18 hours, and then warmed to ambient temperature (25° C.). The mixture was extracted with 0.5N HCl, water, 8% aqueous NaHCO₃, and brine. The organic layer was dried with MgSO₄, filtered, and concentrated in vacuo. The crude product was recrystallized from ethyl acetate to yield 1.2 g of the title compound.

PREPARATION 15

[S-(R R*)-2-[2-[2-(1-tert-Butoxycarbonyl-3-methyl-butylcarbamoyl)-4-fluoro-phenyldisulfanyl]-5-fluoro-benzoylamino]-4-methyl-pentanoic acid tert-butyl ester This compound was prepared according to the general method of Preparation 14 using 2,2'-dithiobis[5-fluorobenzoyl chloride] (2.0 g, 5.2 mmol) in 20 mL dichloromethane, L-leucine,t-butyl ester, monohydrochloride (2.5 g, 11.4. mmol), and N-methyl morpheline (1.4 mL, 12.5 mmol) in 30 mL dichloromethane. The crude product was recrystallized from ethyl acetate to yield 1.8 g of the title compound.

PREPARATION 16

(S-(R*,R*)]-2-[2-[2-(1-tert-Butoxycarbonyl-3-methyl-butylcarbamoyl-5-methyl-phenyldisulfanyl]-4-methyl-benzoylamino]-4-methyl-pentanoic acid tert-butyl ester This compound was prepared according to the general method described in Preparation 14 using 2,2'-dithiobis[4-methylbenzoyl chloride](1.8 g, 7.8 mmol) in 20 mL dichloromethane, L-leucine,t-butyl ester, monohydrochloride (4.0 g, 17.9 mmol), and N-methyl morpholine (4.6 mL, 41 mmol) in 60 mL dichloromethane. The crude product was recrystallized from ethyl acetate to yield 1.9 g of the title compound.

PREPARATION 17

[S-(R*,R*)]-2-[[2-[3-(1-tert-Butoxycarbonyl-3-methyl-butylcarbamoyl)-pyridin-2-yldisulfanyl]-pyridine-3-carbonyl]-amino]-4-methyl-pentanoic acid tert-butyl This compound was prepared according to the general method described in Preparation 14 using 2,2'-dithiobis[3-pyridinecarbonyl chloride] (0.8 g, 2.1 mmol) in 10 mL dichloromethane and L-leucine, t-butyl ester, monohydrochloride (1.5 g, 5.7 mmol) in 20 mL pyridine. The crude product was recrystallized from ethyl acetate to yield 1.9 g of the title compound.

PREPARATION 18

[S-(R*,R*)]-2-[2-[2-(1-Carboxy-2-methylbutyl-carbamoyl) phenyldisulfanyl]-benzoylamino]-3-methyl-pentanoic acid tert-butyl ester A solution of 10.0 g (53.2 mmol) of L-isoleucine t-butyl ester in 100 mL of dichloromethane was mixed with 5.6 g (55.0 mmol) of N-methylmorpholine. The resulting solution was cooled to 0° C. and reacted by rapid dropwise addition of a solution of 8.3 g (24.2 mmol) of 2,2'-dithiobisbenzoyl chloride (from Preparation 1) in 100 mL of dichloromethane, keeping the temperature below 0° C. The mixture was stirred at 0° C. for 1 hour and then stirred at room temperature for 18 hours. The solid which had formed was removed by filtration, washed with water, and dried in vacuo to give 6.5 g of the title compound. The filtrate was washed with water, 0.5M hydrochloric acid, water, dried (MgSO₄), filtered, and evaporated in vacuo to give an additional 6.9 g of the title compound having comparable purity.

PREPARATION 19

[S-(R*,R*)]-2-[2-[2-(1-Carboxy-2-methylbutylcarbamoyl)-phenyldisulfanylbenzoylamino]-3-methyl-pentanoic acid A solution of 13.2 g (20.5 mmol) of the tert-butyl ester (from Preparation 18) in 50 mL of trifluoroacetic acid was stirred at room temperature for 18 hours. The solvent was removed in vacuo, and the residue was dissolved in 50 mL of dichloromethane. The dichloromethane was removed in vacuo, and the residue was triturated with 150 mL of diethyl ether/pentane (2:1 v/v), and the resulting solid was removed by filtration. After washing with 50 mL of diethyl ether/pentane (2:1) and then with pentane, the solid was dried in vacuo and identified as 9.9 g of the title compound, mp 211°–213° C.

PREPARATION 20

[S-(R*,R*)]-2-[2-[2-(1-Carboxy-3-methylbutylcarbamoyl)-5-methoxy-phenyldisulfanyl]-4-methoxybenzoylamino]-4-methyl-pentanoic acid (general method)

A solution of [S-(R*,R*)-2[2-[2-(1-tert-butoxy-carbonyl-3-methylbutylcarbamoyl)-5-methoxy-phenyldisulfanyl]-4-methoxybenzoylamino]-4-methyl-pentanoic acid tert-butyl ester (1.2 g, 1.7 mmol) and anisole (1 mL) in 10 mL dichloromethane, cooled to about 0° C., was treated dropwise with 10 mL of trifluoroacetic acid. The mixture was allowed to warm to ambient temperature. After 4 hours, 5 mL toluene was added, and the solvents were removed in vacuo. The crude product was recrystallized from methanol/water to yield 0.7 g of the title compound.

PREPARATION 21

[S-(R*,R*)]-2-[2-[2-(1-Carboxy-3-methylbutyl-carbamoyl)-4-fluorophenyldisulfanyl]-5-fluorobenzoylamino]-4-methyl-pentanoic acid The general method of Preparation 20 was followed using [S-(R*,R*)]-2-[2-[[2-(1-tert-butoxycarbonyl-3-methylbutylcarbamoyl)-4-fluorophenyldisulfanyl]-5-fluorobenzoylamino]-4-methylpentanoic acid tert-butyl ester (1.8 g, 2.6 mmol) in 20 mL dichloromethane, anisole (2 mL), and 20 mL trifluoroacetic acid. The crude product was recrystallized from methanol/water to afford 0.9 g of the title compound.

PREPARATION 22

[S-(R*,R*)]-2-[2-[-(1-Carboxy-3-methylbutylcarbamoyl)-5-methylphenyldisulfanyl]-4-methylbenzoylamino]-4-methyl-pentanoic acid The general method of Preparation 20 was followed using [S-(R*,R*)]-2-[2-[2-(1-tert-butoxycarbonyl-3-methylbutylcarbamoyl)-5-methylphenyldisulfanyl]-4-methylbenzoylamino]-4-methyl-pentanoic acid tert-butyl ester (1.9 g, 2.8 mmol) in 20 mL dichloromethane, anisole (2.0 mL), and 10 mL trifluoroacetic acid. The crude product was recrystallized from methanol/water to yield 1.1 g of the title compound.

PREPARATION 23

[[S-(R*,R*)]-2-[[2-[3-(1-Carboxy-3-methyl-butylcarbamoyl)-pyridin-2-yl-disulfanyl]-pyridine-3-carbonyl]-amino]-4-methyl-pentanoic acid The general method of Preparation 20 was followed using [S-(R*,R*)]-2-([2-[3-(1-tert-butoxycarbonyl-3-methylbutylcarbamoyl)-pyridin-2-yldisulfanyl]-pyridine-3-carbonyl]-amino)-4-methyl-pentanoic acid tert-butyl ester (1.9 g, 2.9 mmol) in 20 mL dichloromethane, anisole (1.5 mL), and 10 mL trifluoroacetic acid. The crude product was recrystallized from methanol/water to yield 1.2 g of the title compound.

PREPARATION 24

2-Chloro-5-nitrobenzamide

A mixture of 2-chloro-5-nitrobenzoic acid (15.0 g, 74.0 mmol) and 200 mL of dichloromethane was reacted with oxalyl chloride (16.2 mL, 186.0 mmol) and a catalytic amount of dimethylformamide. The mixture was stirred at 25° C. for 3 hours. The solvent was removed in vacuo, and the residue was redissolved in 200 mL of dichloromethane. The solution was cooled to 0° C., and ammonia was bubbled through the cold solution for 5 minutes, whereupon the product precipitated to form solution. The product was collected by filtration to yield 6.8 g, mp 174°–175° C.

PREPARATION 25

2,2'-Dithiobis(5-nitrobenzamide)

To a refluxing solution of 2-chloro-5-nitro-benzamide (6.8 g, 33.0 mmol) from Preparation 24 in 90 mL of ethanol was added portion-wise sodium sulfide hydrate, $Na_2S$ ($9H_2O$) (2.6 g, 20.5 mmol) and sulfur (0.7 g, 20.5 mmol). The mixture was heated at reflux for 1 hour, then cooled to room temperature, whereupon a solid formed. The solid was collected by filtration to yield 2.6 g of the title compound, mp 266°–269° C.

PREPARATION 26

2,2'-Dithiobis(5-aminobenzamide)

2,2'-Dithiobis(5-nitrobenzamide) (2.6 g, 7.0 mmol) was added portion-wise to a refluxing slurry of reduced iron (8.7 g) in 65 mL of water containing 0.1 mL of acetic acid. The resulting slurry was heated at reflux for 2.0 hours, then cooled to room temperature. The slurry was made strongly basic (pH 11) by the addition of 14 mL of 1N NaOH. The alkaline mixture was filtered, and acetic acid was added to the solution to adjust the pH to 7.0. While bubbling oxygen into the solution, a pH=6 to 7 was maintained with the addition of acetic acid. A solid gradually formed as the pH begins to stabilize. The product (1.1 g) was recovered by filtration, mp 188°–190° C.

PREPARATION 27

2,2'-Dithiobis(5-acetylamino)benzamide 2,2'-Dithiobis(5-aminobenzamide) (1.1 g, 3.4 mmol) was dissolved in 6 mL of glacial acetic acid on a steam bath and reacted with acetic anhydride (0.7 mL, 7.2 mmol). Upon cooling, the product precipitated from solution. An additional 4 mL of glacial acetic acid and 0.1 mL of acetic anhydride was added, and the mixture was heated at reflux for 30 minutes, and then cooled to room temperature. The crude product was recovered by filtration and recrystallized from dimethylformamide/dimethyl sulfoxide/water to yield 0.8 g of the title product, mp 301°–303° C.

PREPARATION 28

2,2'-Dithiobis[N-[4-[(acetylamino)sulfonyl]phenyl]-benzamide]

The compound was prepared according to the general method of Preparation 9 using 2,2'-dithiobisbenzoyl chloride (3.0 g, 8.0 mmol) in 30 mL of dichloromethane and 4-[(acetylamino)sulfonyl]aniline (5.6 g, 26.0 mmol) in 100 mL of pyridine. The crude product was purified on a silica gel column using chloroform/methanol (1:1 v/v) as the mobile phase. The pure fractions were pooled, concentrated in vacuo, and the solid was crystallized from ethanol/water (1:1 v/v) to yield 0.5 g of the title compound, mp 180°–182° C.

PREPARATION 29

2-Mercapto-N-(4-sulfamoylphenyl)benzamide 2,2'-Dithiobis[4'-sulfamoylbenzanilide] (0.1 g, 0.2 mmol) was dissolved in 4 mL of dimethylformamide and 1.6 mL of 2.7% aqueous $NaH_2PO_4$. Dithiothreitol (0.1 g, 0.7 mmol) was added, and the mixture was stirred at 25° C. for 0.5 hours. Formic acid (10 mL 10% aqueous) was added to precipitate the product, which was collected by filtration, washed with water, and with diethyl ether to yield 72 mg of the title compound, mp 230°–231° C.

PREPARATION 30

2-[2-[2-(Carboxymethylcarbamoyl)-phenyldisulfanyl]-benzoylamino] acetic acid

To 18 g (0.24 mol) of glycine in 75 mL of absolute ethanol was added 100 mL of a sodium ethoxide solution prepared from dissolution of 4.6 g (0.2 mol) of sodium. The mixture was cooled to –60° C. and 17.2 g (0.05 mol) of 2,2'-dithiobisbenzoyl chloride was added portionwise. The mixture was brought to room temperature and stirred overnight. The solids were removed by filtration, and the filtrate was acidified with 2N HCl. Solids were collected, dissolved in sodium bicarbonate solution, and the solution filtered. The filtrate was acidified with HCl and the solids collected and dried at 110° C. for 24 hours to give 6.8 g of the title compound, mp 13°–215° C.

PREPARATION 31

2-[2-[2-(1-Carboxy-2-methylpropylcarbamoyl)-phenyldisulfanyl]benzoylamino]-3-methylbutanoic acid Using the method employed in Preparation 30, 17.8 g (0.15 mol) of D,L valine was reacted with 17.2 g (0.05 mol) of 2,2'-dithiobisbenzoyl chloride to produce 11.4 g of the title compound after recrystallization from acetic acid, mp 226.5°–227.5° C.

PREPARATION 32

4-[2-[2-(3-Carboxypropylcarbamoyl)phenyldisulfanyl]-benzoylamino] butanoic acid

Following the procedure in Preparation 30, 16 g (0.15 mol) of 4-amino-butanoic acid was reacted with 10.8 g (0.03 mol) of 2,2'-dithiobisbenzoyl chloride to afford 7.14 g of the title compound.

PREPARATION 33

8-Chloro-[1,3]dioxolo[4,5-g]quinoline-7-carboxylic acid (2-pyridin-2-yl-ethyl)-amide To 23.3 g (0.10 mol) of 8-hydroxy-[1,3]-dioxolo[4,5-g] quinoline-7-carboxylic acid (J. Med. Chem., 1968;11:160) in 500 mL of ethylene chloride was added 35 mL (0.47 mol) of thionyl chloride and 1 mL of DMF. The mixture was heated at reflux overnight, concentrated to 100 mL, and the solids collected to give 18.7 g of 8-chloro-[1,3]dioxolo[4,5-g]quinoline-7-carbonyl chloride, which was used without purification. To 13.5 g (~0.05 mol) of this material in 1000 mL of ethylene chloride was added 10 mL (0.07 mol) of triethylamine and the mixture cooled to 15° C. To this mixture was added 6.25 g (0.51 mol) of 2-(2-aminoethyl) pyridine and the mixture was stirred for 24 hours at room temperature. The reaction was quenched by addition of 500 mL H$_2$O. The organic layer was washed with water, dried (MgSO$_4$), and concentrated to give 16 g of the title compound, mp 145°–146° C.

PREPARATION 34

8-Mercapto-[1,3]dioxolo[4,5 9]quinoline-7-carboxylic acid (2-pyridin-2-yl-ethyl)-amide To 10.4 g (0.025 mol) of 8-chloro-[1,3]-dioxolo[4,5-g] guinoline-7-carboxylic acid (2-pyridin-2yl-ethyl)-amide in 100 mL of ethanol was added 7.2 g (0.1 mol) of sodium hydrogensulfide and the mixture was heated at reflux for 3 hours. The mixture was cooled and the solids filtered, washed with ethanol, and then with water. The filtrate was concentrated and the solids were suspended in water, collected by filtration, and recrystallized from ethanol to give 6.8 g of the title compound, mp 258°–260° C.

PREPARATION 35

4-Chloro-2-phenyl-pyrimidine-5-carboxylic acid (2-diethylamino-ethyl)-amide

Using the procedure of Preparation 33, 15.5 g (0.072 mol) of 4-hydroxy-2-phenyl-pyrimidine-5-carboxylic acid (J. Med. Chem., 1964;7:68) was reacted with 8.5 g (0.073 mol) of 2-diethylaminoethylamine to give 18 g of the title compound after recrystallization from benzene, mp 40°–45° C.

PREPARATION 36

4-Mercapto-2-phenyl-pyrimidine-5-carboxylic acid (2-diethylamino-ethyl)-amide

Using the procedure in Preparation 34, 6.4 g (0.02 mol) of 4-chloro-2-phenyl-pyrimidine-5-carboxylic acid (2-diethylamino-ethyl)-amide was reacted with 4.8 g (0.066 mol) of sodium hydrogen sulfide to afford 4.2 g of the title compound, mp 178°–180° C.

PREPARATION 37

5-Chloro-3-methyl-1-phenyl-1H-pyrazole-4-carboxylic acid (2-pyridine-2-yl-ethyl)-amide Using the procedure in Preparation 33, 28.4 g (0.13 mol) of 5-hydroxy-3-methyl-1-phenyl-1H-pyrazole-4-carboxylic acid was reacted with 15.9 g (0.13 mol) of 2-(2-aminoethyl) pyridine to produce the title compound, which was used without purification.

PREPARATION 38

5-Mercapto-3-methyl-1-phenyl-1H-pyrazole-4-carboxylic acid (2-pyridin-2-yl-ethyl) amide Using the procedure of Preparation 34, 29.3 g (0.087 mol) of 5-chloro-3-methyl-1-phenyl-1H-pyrazole-4-carboxylic acid (2-pyridin-2-yl-ethyl)-amide was reacted with 19.3 g (0.27 mol) sodium hydrogen sulfide in cellosolve to give 24.0 g of the title compound, which was used in Example 22 without purification.

PREPARATION 39

4-Chloro-2-dimethylamino-pyrimidine-5-carboxylic acid benzylamide

Using the procedure of Preparation 33, 61.6 g (0.337 mol) of 2-dimethylamino-4-hydroxy-pyrimidine-5-carboxylic acid was reacted with 37 g (0.34 mol) of 2-aminomethyl pyridine to afford 14.3 g of the title compound, which was used without purification.

PREPARATION 40

2-Dimethylamino-4-mercapto-pyrimidine-5-carboxylic acid benzylamide

Using the procedure of Preparation 34, 14.3 g (0.045 mol) of 4-chloro-2-dimethylamino-pyrimidine-5-carboxylic acid benzylamide and 12 g (0.21 mol) of sodium hydrogen sulfide were reacted to give 5.7 g of the title compound, mp 175°–178° C.

PREPARATION 41

4-Chloro-3-phenyl-pyrimidine-5-carboxylic acid benzylamide

Using the procedure of Preparation 33, 31.0 g (0.143 mol) of 4-hydroxy-2-phenyl-pyrimidine-5-carboxylic acid and 60 mL (0.82 mol) of thionyl chloride were reacted to give 37.8 g of crude chloro acid chloride. A 5.0 g (19.8 mmol) portion of the acid chloride was reacted with 2.12 g (19.8 mmol) of benzylamine to give 6.27 g of the title compound, which was used without purification.

PREPARATION 42

4-Mercapto-2-phenyl-pyrimidine-5-carboxylic acid benzylamide

Using the procedure from Preparation 34, 5.8 g (17.9 mmol) of 4-chloro-2-phenyl-pyrimidine-5-carboxylic acid benzylamide was reacted with 5.1 g (72 mmol) of sodium hydrogen sulfide to give 3.75 g of the title compound, mp 189°–193° C.

EXAMPLE 1

4-(3-Oxo-3h-benzo[d]isothiazol-2-yl)-benzenesulfonamide

To a solution of 60 mL of methanol and 60 mL of tetrahydrofuran cooled to 0° C. was added dropwise 3.9 g (30.0 mmol) of chlorocarbonylsulfenyl chloride. The mixture was stirred at 0° C. for 20 minutes and then diluted by addition of 9.0 g (29.2 mmol) of 2-thio-N-(4-sulfamoylphenyl)benzamide. The reaction mixture was stirred at 0° C. for 0.5 hours, warmed to room temperature, and stirred for 18 hours. The suspension was diluted with 200 mL of diethyl ether, stirred for 1 hour, and the solid was removed by filtration. After washing with fresh diethyl ether, the solid was dried in vacuo to give 7.8 g of the title compound. An additional 2.2 g was obtained by concentrating the mother liquors and triturating the residue with diethyl ether. The mp of both fractions was 283°–285° C.

EXAMPLE 2

[S-(R*,R*)]-3-Methyl-2-(3-oxo-3h-benzo[d]isothiazol-3-yl)pentanoic acid

To a stirred suspension of 5.3 g (10.0 mmol) of [S-(R*,R*)]-2-[2-[2-(1-carboxy-2-methylbutylcarbamoyl)-phenyldisulfanylbenzoylamino]-3-methyl-pentanoic acid (from Preparation 19) in 200 mL of dichloromethane was added dropwise 2.4 g (15.0 mmol) of liquid bromine. The reaction mixture was stirred at room temperature for 2 hours and concentrated to dryness in vacuo. The residue was triturated with dichloromethane. The dichloromethane was removed by evaporation in vacuo to remove excess bromine. The residue was partitioned between dichloromethane/5% aqueous sodium bicarbonate (200 mL each). The aqueous layer was separated, washed with fresh dichloromethane, and acidified to pH 1.5 with 6.0M hydrochloric acid. The acidic aqueous solution was extracted with dichloromethane (2×75 mL). The organic layers were combined, washed with water, dried (MgSO$_4$), filtered and concentrated to dryness in vacuo to give 4.8 g of the title compound, mp 50°–52° C.

EXAMPLE 3

N-Acetyl-4-(3-oxo-3h-benzo[d]isothiazol-2-yl)-benzenesulfonamide

A solution of 2,2'-dithiobis-N-[4-[[acetylamino]-sulfonyl]phenyl]benzamide (1.0 g, 1.5 mmol) in 1 mL dimethylformamide was diluted with 20 mL dichloromethane, whereupon a fine precipitate formed. Bromine (0.3 g, 1.8 mmol) in 5 mL dichloromethane was added dropwise to the mixture. A homogenous solution gradually formed, and then a solid reformed. The solid was collected by filtration and recrystallized from acetic acid/water (1:1 v/v) to afford 0.6 g of the title compound, mp 254°–255° C.

EXAMPLE 4

N-(3-Oxo-2,3-dihydro-benzo[d]isothiazol-5-yl)-acetamide

Following the general method of Example 3, a slurry of 2,2'-dithiobis[5-acetylamino]benzamide (2.0 g, 4.8 mmol) in 4 mL dimethyl sulfoxide and 20 mL dichloromethane was reacted with bromine (0.8 g, 5.0 mmol) in 10 mL of dichloromethane. The solid product was collected by filtration and recrystallized from 5 mL of hot acetic acid to yield 0.8 g of the title compound.

EXAMPLE 5

4-(5-Methoxy-3-oxo-3h-benz[d]isothiazol-2-yl)-benzenesulfonamide

Following the general method of Example 3, a slurry of 2,2'-dithiobis(4-sulfamoyl(5-methoxy-benzanilide)) (0.8 g, 1.2 mmol) in 2 mL dimethylformamide and 20 mL dichloromethane was reacted with bromine (0.2 g, 1.3 mmol) in 10 mL dichloromethane. The crude product was recrystallized from methanol/water to afford 0.2 g of the title compound.

EXAMPLE 6

4-(6-Methyl-3-oxo-3h-benzo[d]isothiazol-2-yl)-benzenesulfonamide

Following the general method of Example 3, a slurry of 2,2'-dithiobis[4'-sulfamoyl(4-methyl-benzanilide)] (2.1 g, 3.2 mmol) (from Preparation 11) in 4 mL dimethylformamide/40 mL dichloromethane was reacted with bromine (0.6 g, 3.6 mmol) in 15 mL dichloromethane. The crude product was recrystallized from dimethylformamide/water to yield 0.9 g of the title compound.

EXAMPLE 7

4-(6-Fluoro-3-oxo-3h-benzo[d]isothiazol-2-yl)-benzenesulfonamide

Following the general method of Example 3, a slurry of 2,2'-dithiobis[4'-sulfamoyl(4-fluoro-benzanilide)] (1.8 g, 2.7 mmol) (from Preparation 12) in 4 mL dimethylformamide and 30 mL dichloromethane was reacted with bromine (0.5 g, 3.2 mmol) in 20 mL of dichloromethane. The crude product was recrystallized from dimethylformamide/water to yield 1.1 g of the title compound, mp 265°–266° C.

EXAMPLE 8

4-(5-Methyl-3-oxo-3h-benzo[d]isothiazol-2-yl)-benzenesulfonamide

Following the general method of Example 3, a slurry of 2,2'-dithiobis[4'-sulfamoyl(5-methyl-benzanilde)] (1.1 g, 1.7 mmol) (from Preparation 13) in 2 mL dimethylformamide and 20 mL dichloromethane was treated with bromine (0.3 g, 1.9 mmol) in 10 mL dichloromethane. The crude compound was recrystallized from dimethylformamide/water to afford 0.4 g of the title compound.

EXAMPLE 9

(S)-4-Methyl-2-(6-methoxy-3-oxo-3h-benzo[d]isothiazol-2-yl)-pentanoic acid

Following the general method of Example 3, a slurry of [[s-(R*,R*)]-2-[2-[2-(1-carboxy-3-methyl-butylcarbamoyl)-5-methoxyphenyldisulfanyl]-4-methoxybenzoylamino)]-4-methyl-pentanoic acid (1.4 g, 2.3 mmol) (from Preparation 20) in 4 mL of acetonitrile and 10 mL dichloromethane was treated with bromine (0.4 g, 2.6 mmol) in 10 mL dichloromethane. The crude product was recrystallized from methanol/water to afford 0.8 g of the title compound.

EXAMPLE 10

(S)-4-Methyl-2-(5-fluoro-3-oxo-3h-benzo[d]
isothiazol-2-yl)-pentanoic acid

Following the general method of Example 3, a slurry of [s-(R*,R*)]-2-[-[2-(1-carboxy-3-methyl-butylcarbamoyl)-4-fluorophenyldisulfanyl]-5-fluorobenzoylamino]-4-methyl-pentanoic acid (2.1 g, 3.6 mmol) (from Preparation 21) in 8 mL acetonitrile and 25 mL dichloromethane was treated with bromine (0.7 g, 4.4 mmol) in 15 mL dichloromethane. The crude compound was recrystallized from methanol/water to afford 1.4 g of the title compound, mp 161°–162° C.

EXAMPLE 11

(S)-4-Methyl-2-(6-methyl-3-oxo-3h-benzo[d]
isothiazol-2-yl)-pentanoic acid

Following the general method of Example 3, a slurry of [s-(R*,R*)]-2-[-[2-(1-carboxy-3-methyl-butylcarbamoyl)-4-methylphenyldisulfanyl]-5-methylbenzoylamino]-4-methyl-pentanoic acid (1.8 g, 3.2 mmol) (from Preparation 22) in 5 mL acetonitrile and 20 mL dichloromethane was reacted with bromine (0.6 g, 3.7 mmol) in 10 mL dichloromethane. The crude product was recrystallized from methanol/water to afford 1.3 g of the title compound.

EXAMPLE 12

(S)-4-Methyl-2-(3-oxo-3h-isothiazolo[5,4-b]pyridin-2-yl)-pentanoic acid

Following the general method of Example 3, a slurry of {[S-(R*,R*)]-2-(2-[3-(1-carboxy-3-methyl-butylcarbamoyl)-pyridin-2-yl-disulfanyl]-pyridine-3-carbonyl}-amino)-4-methyl-pentanoic acid (2.1 g, 4.1 mmol) (from Preparation 23) in 3 mL acetonitrile and 10 mL dichloromethane was reacted with bromine (0.3 g, 1.8 mmol) in 8 mL dichloromethane. The crude compound was recrystallized from methanol/water to yield 0.3 g of the title compound.

EXAMPLE 13

2-(3-Oxo-3h-benzo[d]isothiazol-2-yl)acetic acid

To 6.0 g (13.3 mmol) of 2-[2-[2-carboxylmethyl-carbamoyl]phenyldisulfanyl]benzoylamino] acetic acid (from Preparation 30) suspended in 50 mL of CCl$_4$ was added dropwise 0.83 mL (16.1 mmol) of bromine in 15 mL of CCl$_4$ over 1 hour. The solids were removed by filtration. A 6.0 g portion was heated at reflux in 25 mL of acetic acid for 1 hour. The mixture was cooled, and the solids were collected by filtration. Recrystallization from 90% methyl cellosolve, followed by drying at 50° C. for 24 hours gave 3.0 g of the title compound, mp 236°–238° C.

EXAMPLE 14

3-Methyl-2-(3-oxo-3h-benzo[d]isothiazol-2-yl)-butanoic acid

Following the procedure of Example 13, 6.0 g (13.6 mol) of 2-[2-[2-(1-carboxy-3-methylbutyl-carbamoyl)phenyldisulfanyl]benzoylamino]-3-methylbutanoic acid was reacted with bromine to provide 2.25 g of the title compound, mp 166°–168° C.

EXAMPLE 15

2-Phenyl-3-oxo-3h-benz[d]isothiazole

Using the procedure from Example 13, 20 g (43.7 mmol) of 2,2'-dithiobisbenzanilide (prepared as described in *J. Med. Chem.*, 1985;28:1772) was reacted with bromine to give 10.55 g of crude isothiazole. Crystallization from absolute ethanol, and then isopropanol gave 5.4 g of 3-phenyl-3-oxo-3h-benz[d]-isothiazole, mp 143°–145° C.

EXAMPLE 16

2-(4-Acetylphenyl)-3-oxo-3h-benz[d]isothiazole

To 7.0 g (12.9 mmol) of 2,2'-dithiobis[4'48-acetyl (benzanilide)] in 50 mL of CCl$_4$ was added dropwise over 1 hour a solution of 0.7 mL (13.5 mmol) of bromine in 5 mL of CCl$_4$. The solid precipitate was collected by filtration. A 1.3 g portion of the solid was slurried in sodium bicarbonate solution for 30 minutes. The solid was collected by filtration and dried at 70° C. for 24 hours to give 0.87 g of the title compound, mp 183°–185° C.

EXAMPLE 17

4-(3-Oxo-2-h-benzo[d]isothiaz-2-yl-butanoic acid

Using the procedure from Example 13, 2.4 g (5.0 mmol) of 4-[2-[2-(3-carboxypropylcarbamoyl) phenyldisulfanyl] benzoylamino]-butanoic acid (from Preparation 32) was reacted with bromine to give 0.85 g of the crude isothiazolone, which was recrystallized from isopropanol to give 0.76 g of the title compound, mp 97°–99° C.

EXAMPLE 18

2-(4-Methylpyridin-2-yl)-3-oxo-3h-benzo[d]
isothiazole

Using the method of Fischer and Hurni (*Arzneimittel Forsch.*, 1964;14:1301) 5.4 g (0.05 mol) of 2-amino-4-methylpyridine in 50 mL of pyridine at 10° C. was reacted with 10.3 g (0.05 mol) of 2-chloro-sulfenylbenzoyl chloride. The mixture was heated to 50° C. and maintained at that temperature for 2 hours. The mixture was cooled to 25° C. and filtered. The solid was recrystallized from benzene to give 4.5 g of the title compound, mp 195°–196.5° C.

EXAMPLE 19

4-(3-Oxo-3h-benzo[d]isothiazol-2-yl) phenylacetic
acid

To a mixture of 7.55 g (0.05 mol) of 4-amino-phenylacetic acid and 15.15 g (0.15 mol) of triethyl-amine in 25 mL of ethyl cellosolve was added 10.3 g (0.05 mol) of 2-chlorosulfenylbenzoyl chloride (*Arzneimittel Forsch.*, 1964;14:1301). The mixture was stirred at room temperature for 3 hours, concentrated in vacuo, and water was added to the residue. The mixture was acidified with HCl and filtered to give 9.9 g of the title compound, mp 173°–175° C.

EXAMPLE 20

2-[2-(2-Pyridinyl)ethyl]-[1,3]dioxolo[4,5-g]-
isothiazolo[4,5-c]quinolin-3(2H)-one To 4.1 g (0.012 mol) of 8-mercapto-[1,3]dioxolo-[4,5-g] quinoline-7-carboxylic acid (2-pyridin-2-yl-ethyl)-amide (from Preparation 34) and 5 mL (0.035 mol) of triethylamine in 750 mL of methanol was added 2.95 g (0.012 mol) of iodine in 100 mL of methanol. The mixture was heated at reflux for 2 hours, cooled, and then concentrated to an oil. The residue was slurried in water, and the solid was collected and recrystallized in ethanol to give 3.5 g of the title compound, mp 200°–201° C.

EXAMPLE 21

2-2-(Diethylamino)ethyl]-6-phenyl-isothiazolo[5,4-d]pyrimidin-3(2H)-one

Using the procedure of Example 20, 3.3 g (0.01 mol) of 4-mercapto-2-phenyl-pyrimidine-5-carboxylic acid (2-diethylamino-ethyl)-amide (from Preparation 36) and 2.54 g (0.01 mol) of iodine were reacted to give 2.25 g of the title compound after recrystallization from isopropanol, mp 106°–107° C.

EXAMPLE 22

3-Methyl-1-phenyl-5-[2-(2-pyridinyl)ethyl]-1H-pyrazolo[4,5-d]isothiazol-4(5H)-one Using the procedure of Example 20, 24 g (0.069 mol) of 5-mercapto-3-methyl-1-phenyl-1H-pyrazole-4-carboxylic acid (2-pyridin-2-yl-ethyl)amide (from Preparation 38) was reacted with 17.6 g (0.069 mol) of iodine to give 4.8 g of the title compound after two recrystallizations from isopropanol, mp 137°–138° C.

EXAMPLE 23

6-(Dimethylamino)-2-(2-pyridinylmethyl)isothiazolo-[5,4-d]pyrimidin-3-(2H)-one Using the procedure of Example 20, 5.7 g (0.02 mol) of 2-dimethylamino-4-mercapto-pyrimidine-5-carboxylic acid benzylamide (from Preparation 40) was reacted with 5.0 g (0.02 mol) of iodine to give 2.27 g of the title compound after crystallization from ethanol, mp 145°–146° C.

EXAMPLE 24

2-Benzyl-6-phenyl-isothiazolo[5,4-d]pyrimidin-3-one

Using the procedure of Example 20, 2.0 g (6.22 mmol) of 4-mercapto-2-phenyl-pyrimidine-5-carboxylic acid benzylamide (from Preparation 42) was reacted with 1.74 g (6.8 mmol) of iodine to give 1.74 g of the title compound after crystallization from isopropanol, mp 166°–167° C.

EXAMPLE 25

4-(3-Oxo-3h-benz-[d]isothiazol-2-yl)-phenylacetic acid

Using the procedure of Example 13, 1.5 g (2.6 mmol) of 4-[2-[2-(4-carboxymethylphenylcarbamoyl)-phenyldisulfanyl]benzoylamino]phenylacetic acid was reacted with bromine to give 0.62 g of the title compound, mp 173°–175° C.

EXAMPLE 26

(S)-2,6-Bis-(3-oxo-3H-benzo[d]isothiazol-2-yl)-hexanoic acid methyl ester

Using the procedure from Example 18, 0.77 g (3.3 mmol) of lysine methyl ester dihydrochloride and 2.1 mL (15 mmol) of triethylamine in 60 mL of dichloromethane was reacted with 1 g (3.0 mmol) of 2-chlorosulfenylbenzoyl chloride. The mixture was stirred at room temperature for 18 hours, then the solution was washed with 1N HCl, saturated $NaHCO_3$, and brine. The solution was dried and concentrated to give 1 g of an oil. The compound was purified by chromatography ($SiO_2$, $CHCl_3$-$CHCl_3$/MEOH; 98/2) to give 0.16 g of the title compound as a glass. NMR (DMSO): δ 8.03 (m, 2H), 7.61 (m, 2H), 7.50 (m, 2H), 7.41 (m, 2H), 5.42 (m, 1H), 3.88 (t, 2H), 3.75 (s, 3H), 2.24 (m, 1H, 2.11 (m, 1H, 1.87 (m, 2H), 1.44 (m, 2H).

EXAMPLE 27

2-(2-Morpholin-4-yl-ethyl)-6-phenyl-isothiazolo[5,4-d)pyrimidin-3-one

Using the procedure of Example 20, 2.0 g (5.81 mmol) of 4-mercapto-2-phenyl-pyrimidine-5-carboxylic acid (2-morpholin-4-yl-ethyl)-amide were treated with 1.47 g (5.81 mmol) of iodine to give 1.21 g of the title compound after recrystallization from isopropanol, mp 163°–165° C.

EXAMPLE 28

2-Phenethyl-6-phenyl-isothiazolo[5,4-d]-pyrimidin-3-one

Using the procedure of Example 20, 2.0 g (5.96 mmol) of 4-mercapto-2-phenyl-pyrimidine-5-carboxylic acid phenethyl-amide were treated with 1.66 g (6.56 mmol) of iodine to give 1.42 g of the title compound after recrystallization from isopropanol, mp 144°–147° C.

EXAMPLE 29

6-Phenyl-2-pyridin-2-ylmethyl-isothiazolo[5,4-d]-pyrimidin-3-one

Using the procedure of Example 20, 2.0 g (6.20 mmol) of 4-mercapto-2-phenyl-pyrimidine-5-carboxylic acid (pyridin-2-ylmethyl)-amide were treated with 1.73 g (6.82 mmol) of iodine to give 1.62 g of the title compound after recrystallization from isopropanol, mp 154°–156° C.

EXAMPLE 30

6-Phenyl-2-(2-pyridin-2-yl-ethyl)-isothiazolo[5,4-d]-pyrimidin-3-one

Using the procedure of Example 20, 14.0 g (41.6 mmol) of 4-mercapto-2-phenyl-pyrimidine-5-carboxylic acid (2-pyridin-2-yl-ethyl)-amide were treated with 10.6 g (41.7 mmol) of iodine to give 12.7 g of the title compound after recrystallization from ethanol, mp 132°–133° C.

EXAMPLE 31

6-Piperidin-1-yl-2-(2-pyridin-2-yl-ethyl)-isothiazolo[5,4-d]pyrimidin-3-one

Using the procedure of Example 20, 33.0 g (96.2 mmol) of 4-mercapto-2-piperidin-1-yl-pyrimidine-5-carboxylic acid (2-pyridin-2-yl-ethyl)-amide were treated with 24.4 g (96.1 mmol) of iodine to give 21.4 g of the title compound after recrystallization from aqueous ethanol, mp 109°–110° C.

EXAMPLE 32

6-Piperidin-1-yl-isothiazolo[5,4-d]pyrimidin-3-one

Using the procedure of Example 20, 20.8 g (87.4 mmol) of 4-mercapto-2-piperidin-1-yl-pyrimidine-5-carboxylic acid amide were treated with 22.2 g (87.4 mmol) of iodine to give 14.37 g of the title compound after recrystallization from dimethyl-formamide, mp 268°–269° C.

EXAMPLE 33

6-Morpholin-4-yl-2-(2-piperidin-1-yl-ethyl)-isothiazolo[5,4-d]pyrimidin-3-one Using the procedure of Example 20, 5.2 g (14.8 mmol) of 4-mercapto-2-morpholin-4-yl-pyrimidine-5-carboxylic acid (2-piperidin-1-yl-ethyl)-amide were treated with 3.81 g (15.0 mmol) of iodine to give 2.6 g of the title compound after recrystallization from aqueous isopropanol, mp 98°–100° C.

EXAMPLE 34

6-Dimethylamino-2-(2-pyridin-2-yl-ethyl)-isothiazolo[5,4-d]pyrimidin-3-one

Using the procedure of Example 20, 7.5 g (24.8 mmol) of 2-dimethylamino-4-mercapto-pyrimidine-5-carboxylic acid (2-pyridin-2-yl-ethyl)-amide were treated with 6.4 g (25.2 mmol) of iodine to give 4.21 g of the title compound after recrystallization from isopropanol, mp 134°–136° C.

EXAMPLE 35

6-Dimethylamino-2-(2-piperidin-1-yl-ethyl)-isothiazolo[5,4-d]pyrimidin-3-one Using the procedure of Example 20, 6.2 g (20.1 mmol) of 2-dimethylamino-4-mercapto-pyrimidine-5-carboxylic acid (2-piperidin-1-yl-ethyl)-amide were treated with 5.08 g (20.0 mmol) of iodine to give 5.31 g of the title compound after recrystallization from ethyl acetate, mp 128°–129° C.

Additional isothiazolones which can be made utilizing the processes described above include the following:

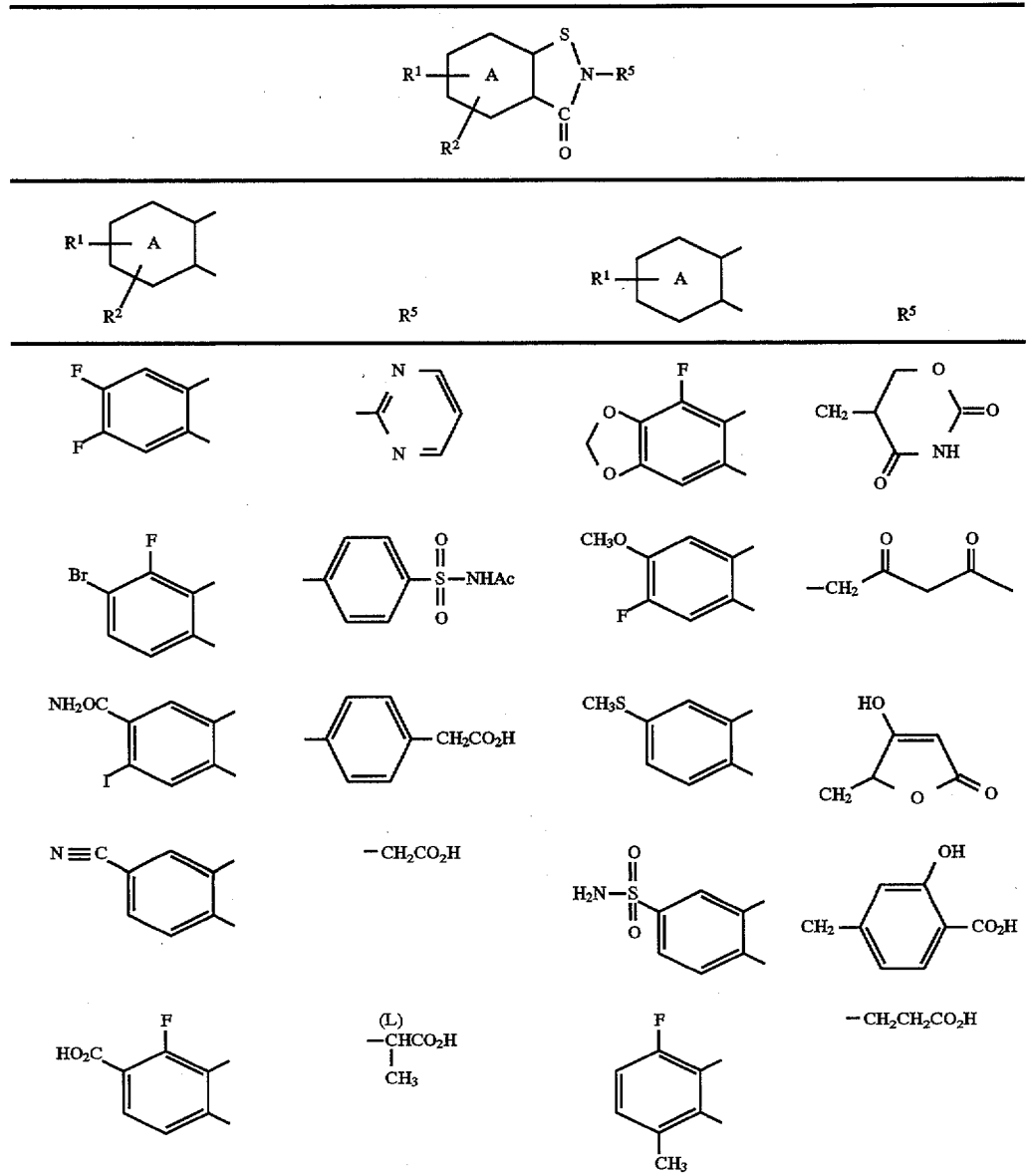

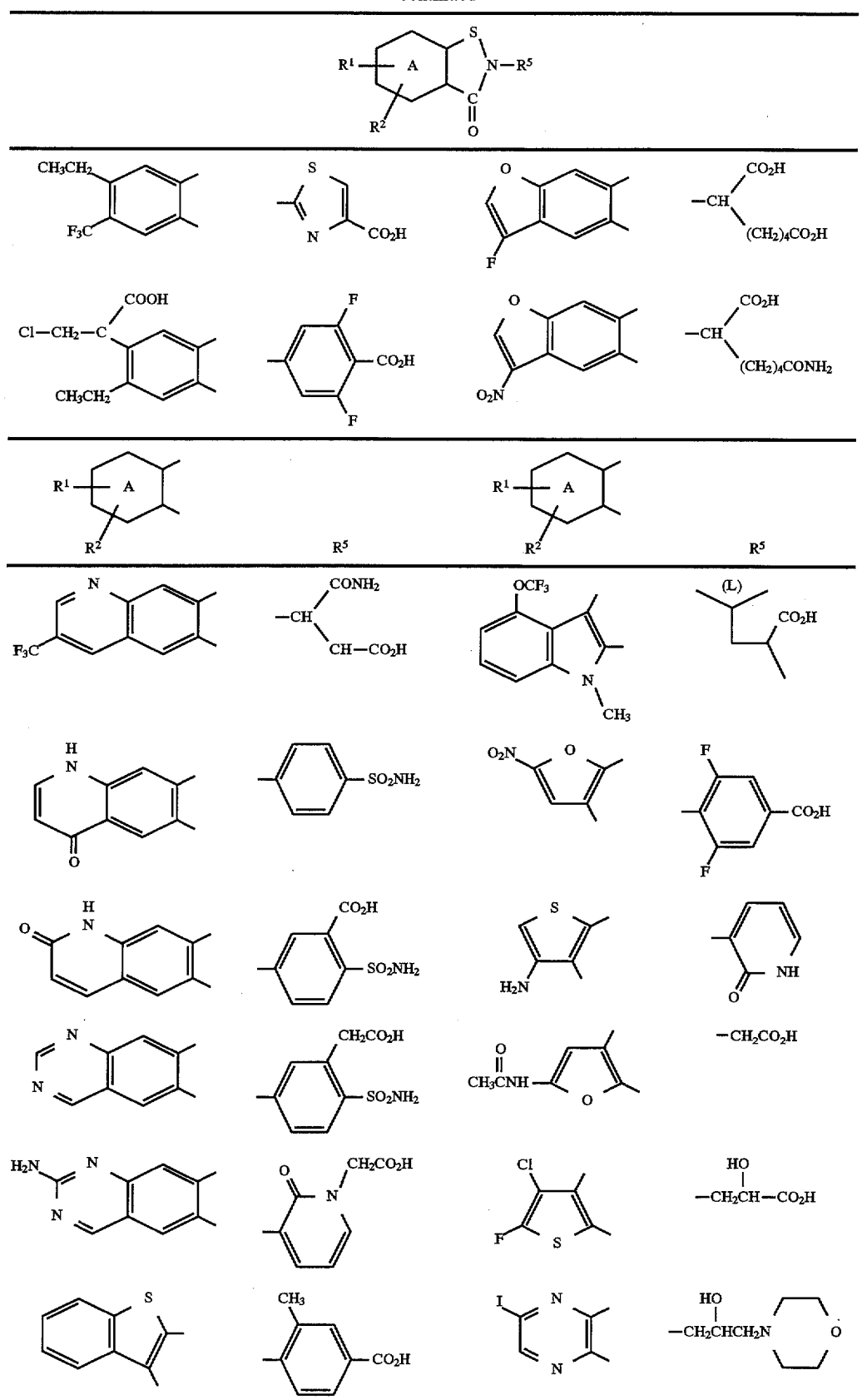

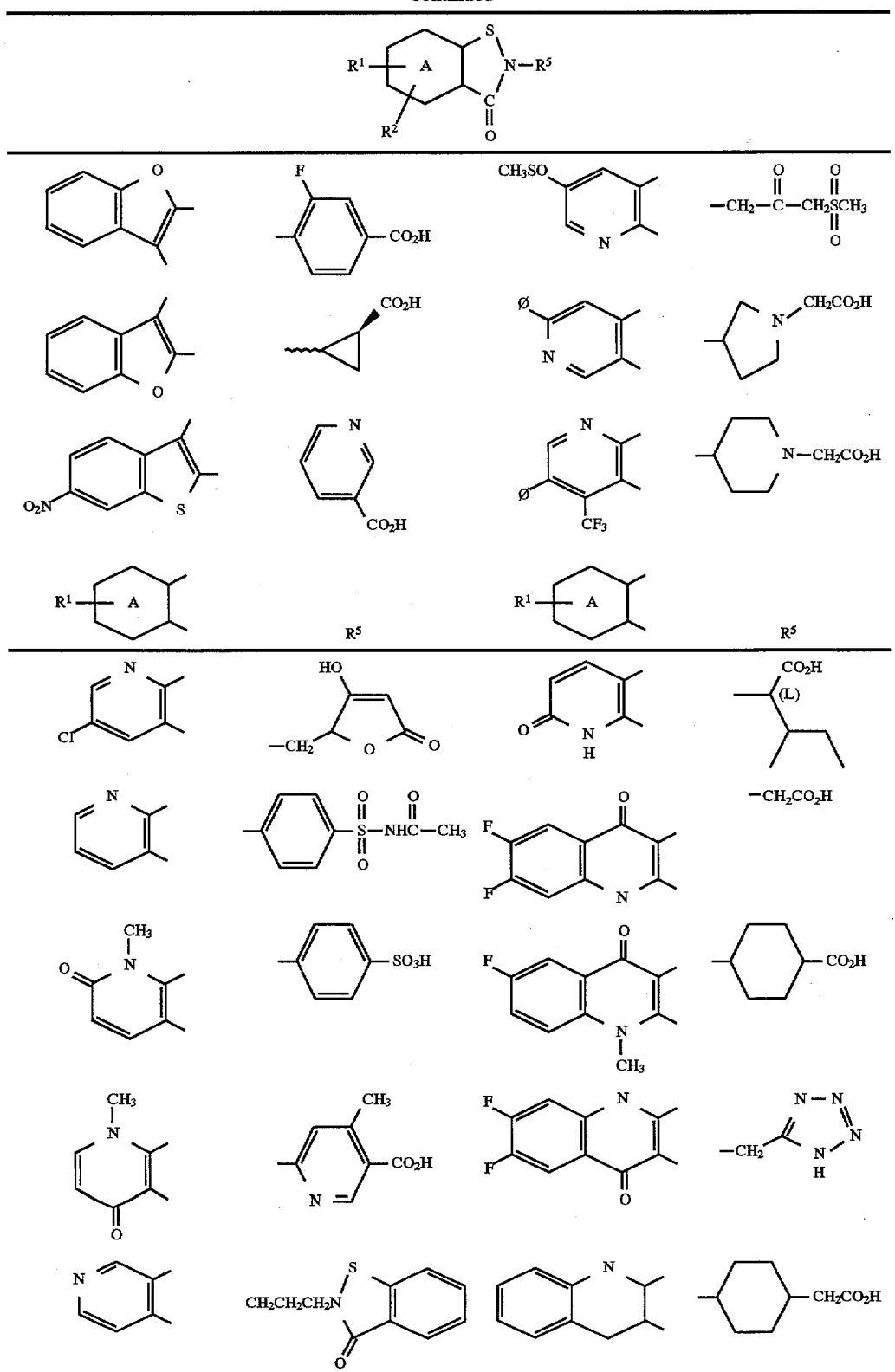
Additional specific isothiazolones according to this invention include the following:

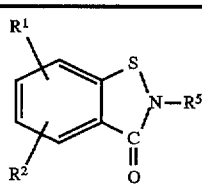

| Example | R¹ | R² | R⁵ |
|---|---|---|---|
| 36 | H | H | —CHiPrCOOH |
| 37 | H | H | n-hexyl |
| 38 | H | H | —CH₂COOEt |
| 39 | H | H | -phenyl |
| 40 | H | H | 4-acetylphenyl |
| 41 | H | H | acetyl |
| 42 | H | H | benzoyl |
| 43 | H | H | C(S)NH phenyl |
| 44 | H | H | 4-chlorobenzoyl |
| 45 | H | H | 4-nitrobenzoyl |
| 46 | H | N | CO(CH₂)₄CH₃ |
| 47 | H | H | COCH₂ phenyl |
| 48 | H | H | COCH₂—N(phthalimido) |
| 49 | H | H | 4-methoxybenzoyl |
| 50 | H | H | 1-hydroxycarbonyl-2-methylbutyl |
| 51 | H | H | 2-ethoxycarbonylbenzoyl |
| 52 | H | H | 2-chlorobenzoyl |
| 53 | H | H | 4-methyl-2-pyridyl |
| 54 | H | H | 5-nitrothiazolon-2-yl |
| 55 | H | H | 2-(4-nitrophenyl)-2-hydroxy-1-hydroxymethylethyl |
| 56 | H | H | 3-hydroxycarbonylpropyl |
| 57 | H | H | 2-hydroxycarbonylbenzyl |
| 58 | H | H | 2-pyrrolidin-1-ylethyl |
| 59 | 5-CH₃O | 6-CH₃O | 2-(2-pyridyl)ethyl |
| 60 | H | H | 2-(2-piperidyl)ethyl |
| 61 | H | H | 3-(1-piperidyl)propyl |
| 62 | H | H | 4-hydroxycarbonylmethylphenylbenzyl |
| 63 | H | H | 4-methoxybenzyl |
| 64 | H | H | 4-methoxyphenyl |
| 65 | H | H | 2,4-dichlorophenyl |
| 66 | H | H | 2,4-dichlorobenzyl |
| 67 | H | H | 3,4-dichlorophenyl |
| 68 | H | H | 3,4-dichlorobenzyl |
| 69 | H | H | 4-chlorophenyl |
| 70 | H | H | 4-chlorobenzyl |
| 71 | H | H | 4-(N-acetylamino)-phenyl |
| 72 | H | H | 4-(N-acetylamino)-benzyl |
| 73 | H | H | 4-ethoxycarbonylphenyl |
| 74 | H | H | 4-ethoxycarbonylbenzyl |
| 75 | H | H | 4-tert-butylphenyl |
| 76 | H | H | 4-tert-butylbenzyl |
| 77 | H | H | 4-trifluoromethylphenyl |
| 78 | H | H | 4-trifluoromethylbenzyl |
| 79 | H | H | 4-biphenyl |
| 80 | H | H | 4-phenylbenzyl |
| 81 | H | H | 4-nitrobenzyl |
| 82 | H | H | cyclopropyl |
| 83 | H | H | cyclopropylmethyl |
| 84 | H | H | 2-phenylethyl |
| 85 | H | H | cyclohexyl |
| 86 | H | H | cyclohexylmethyl |
| 87 | H | H | 4-aminosulfonylphenyl |

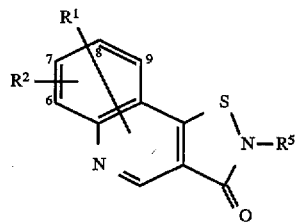

| Example | R¹ | R² | R⁵ | mp °C. |
|---|---|---|---|---|
| 88 | H | H | n-propyl | |
| 89 | H | H | 2-(2-pyridyl)-ethyl | |
| 90 | H | H | 2-(N,N-diethyl-amino)ethyl | |
| 91 | 7-chloro | 8-chloro | 2-dimethylaminoethyl | 241–242 |
| 92 | 6-methoxy | 9-chloro | 2-dimethylaminoethyl | 172–173 |
| 93 | H | 7-methoxy | 2-dimethylaminoethyl | 175–176 |
| 94 | H | 8-methoxy | 2-dimethylaminoethyl | 155–156 |
| 95 | | 7,8-methylenedeoxy | 3-dimethylaminopropyl | 160–161 |
| 96 | | 7,8-methylenedeoxy | 2-pyrrolidinoethyl | 185–186 |
| 97 | | 7,8-methylenedeoxy | 2-morpholinoethyl | 200–202 |
| 98 | H | 8-chloro | 2-dimethylaminoethyl | 214–215 |
| 99 | | 7,8-methylenedeoxy | 2-acetamidoethyl | >260 |
| 100 | 7-chloro | 8-methoxy | 2-dimethylaminoethyl | 226–227 |

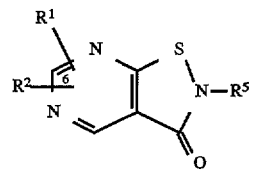

| Example | R¹ | R² | R⁵ |
|---|---|---|---|
| 101 | H | 6-piperidino | 2-(N,N-diethylamino)ethyl |
| 102 | H | 6-piperidino | 2-(2-pyridyl)ethylhydrochloride |
| 103 | H | 6-dimethylamino | 2-piperidylmethyl |
| 104 | H | 6-pyrrolidino | 2-(2-pyridyl)ethyl |

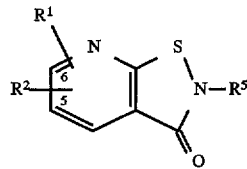

| Example | R¹ | R² | R⁵ |
|---|---|---|---|
| 105 | H | 6-phenylsulfonyl | 2-dimethylaminoethyl |
| 106 | H | 6-chloro | methyl |
| 107 | H | 6-trifluoromethyl | cyclopropyl |
| 108 | H | 6(3,4-dimethoxyphenyl) | 2-dimethylaminoethyl |

-continued

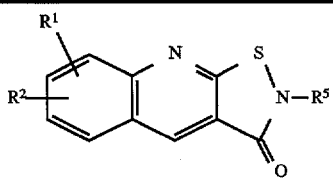

| Example | R¹ | R² | R⁵ | mp °C. |
|---|---|---|---|---|
| 109 | H | H | 2-dimethylaminoethyl | 86–87 |

As can be seen from the foregoing, this invention contemplates the use of any compound which falls within the generic term "isothiazolone" as defined herein. All that is required to lower plasma levels of Lp(a) according to this invention is to administer to an animal an Lp(a) lowering amount of an isothiazolone. All of the isothiazolones to be utilized are either known or are readily prepared as described above.

We have evaluated several specific isothiazolones for their ability to inhibit the formation of Lp(a) and thereby to lower Lp(a) levels in animals. The compounds can be evaluated according to several protocols.

A standard in vitro assay was utilized to measure inhibition of Lp(a) particle formation. The assay was carried out by combining 45 µL of recombinant apolipoprotein(a) and 45 µL of a low density lipoprotein (LDL) source with 10 µL of a 1% aqueous dimethylsulfoxide solution containing a test compound. Various concentrations of test compound were evaluated (ranging from 1 to 50 µM) in order to determine the dose of compound required to inhibit the formation of the Lp(a) particle by 50% (the IC$_{50}$). Each dose level was evaluated in triplicate. The test solutions, and a control solution containing all reactants except a test compound, were added to individual wells of 96-well microtiter plate. The microtiter plate was incubated at 37° C. for 30 minutes. Lp(a) levels were measured in each well utilizing a two-antibody, sandwich enzyme-linked immunosorbent assay (ELISA). The assay employs a mouse monoclonal anti-human Lp(a) capture antibody, and a rabbit anti-human apo B-100 detection antibody. Inhibition of Lp(a) particle formation by test compound was calculated relative to control reactions in which Lp(a) formation was set at the 100% level. When evaluated according to the foregoing assay, the compound of Example 2 exhibited an IC$_{50}$ of 29.5 µM.

Another in vitro assay is carried out by mixing approximately equal quantities of recombinant human apo(a) with low-density lipoprotein (LDL) in a 0.5 µL microcentrifuge tube. Control vessels contained no invention compound, whereas test vessels contained a compound of Formula I at a concentration of either 5 µM or 25 µM. The mixtures were incubated at 37° C. for 30 minutes. The coupling between apo(a) and LDL was quenched by addition of sodium dodecylsulfate (SDS)-PAGE loading buffer. The mixture is next resolved on 4% polyacrylamide gels, and Lp(a) is detected by western blotting using a monospecific human Lp(a) antibody. The intensity of the Lp(a) bands on the blots is measured by a commercial densitometer.

When evaluated in this assay, the compound of Example 2 inhibited Lp(a) formation 25.5% at 5 µM, and 41.3% at 25 µM.

For use in the method of this invention, the isothiazolones preferably are combined with one or more pharmaceutically acceptable diluents, carriers, excipients, or the like, for convenient oral, parenteral, and topical administration to animals, preferably humans. The isothiazolones are ideally suited to formulation for oral administration in the form of tablets, capsules, dispersible powders, granules, suspensions, elixirs, buccal seals, and the like. The formulations typically will contain from about 1% to about 90% by weight of active isothiazolone, and more commonly from about 5% to about 60% by weight.

Oral formulations can contain, for suspensions, from about 0.05% to about 5% by weight of a suspending agent, such as talc or the like, and syrups will contain from about 10% to about 50% by weight of a sugar such as dextrose. Tablets may contain normal amounts of binders, stabilizers, and common diluents such as corn starch and sugars. Parenteral formulations, for instance, solutions for IV injection, will be made by dissolving or suspending the isothiazolone in a solvent such as isotonic saline or 5% glucose in sterile water.

The dose of isothiazolone to be administered is that amount which is effective for lowering plasma levels of Lp(a) in an animal.

The effective dosage of active ingredient employed may vary depending on the particular compound employed, the mode of administration, and the severity of the condition being treated. However, in general, satisfactory results are obtained when the isothiazolones are administered at a daily dosage of from about 0.5 to about 500 mg/kg of animal body weight, preferably given in divided doses two to four times a day, or in sustained-release form. For most large mammals, such as humans, the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The isothiazolones may be administered orally as well as by intravenous, intramuscular, or subcutaneous routes. Solid carriers include starch, lactose, dicalciumphosphate, microcrystalline cellulose, sucrose, and kaolin, while liquid carriers include sterile water, polyethylene glycols, nonionic surfactants, and edible oils such as corn, peanut, and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT, and BHA. The preferred pharmaceutical compositions from the stand point of ease of preparation and administration are solid compositions, particularly tablets and hard-filled or liquid-filled capsules. Oral administration of the compounds is preferred. These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacterial and fungi: The carrier can be a solvent or dispersion medium containing, for example, water, ethanol, polyol (e.g., glycerol, propylene glycol, and liquid polyethylene glycol), suitable mixtures thereof, and vegetable oils.

The compounds may also be encapsulated in liposomes to allow an intravenous administration of the drug. The liposomes suitable for use in the invention are lipid vesicles and may include plurilamellar lipid vesicles, small sonicated multimellar vesicles, reverse phase evaporation vesicles, large multilamellular vesicles, and the like, wherein the lipid vesicles are formed by one or more phospholipids such as phosphotidylcholine, phosphatidylglycerol, sphingomyelin, phospholactic acid, and the like. In addition, the liposomes may also comprise a sterol component such as cholesterol.

Some typical formulations which can be administered to humans are as follows:

Tablet Formulation

The compound of Example 9 (250 mg) is blended to uniformity with 100 mg of corn starch and 50 mg of lactose. The mixture is compressed into a tablet. Such tablets are administered orally at the rate of one to three times a day.

Preparation of Oral Suspension

| Ingredient | Amount |
| --- | --- |
| Compound of Example 13 | 500 mg |
| Sorbitol solution (70% NF) | 40 mL |
| Sodium benzoate | 150 mg |
| Saccharin | 10 mg |
| Red dye | 10 mg |
| Cherry flavor | 50 mg |
| Distilled water qs OD | 100 mL |

The sorbitol solution is added to 40 mL of distilled water and the isothiazolone is suspended thereon. The saccharin, sodium benzoate, flavor, and dye are added and dissolved. The volume is adjusted to 100 mL with distilled water. Each milliliter of syrup contains 5 mg of isothiazolone.

Suppositories

A mixture of 400 mg of the compound of Example 23 and 600 mg of theobroma oil is stirred at 60° C. to uniformity. The mixture is cooled and allowed to harden in a tapered mold to provide a 1-g suppository.

Parenteral Solution

In a solution of 700 mL of propylene glycol and 200 mL of sterile water is suspended 20.0 g of the compound of Example 35. The pH is adjusted to pH 6.5 with dilute sodium hydroxide, and the volume is made up to 100 mL with water for injection. The formulation is sterilized, filled into 5.0-mL ampoules each containing 2.0 mL (representing 40 mg of drug), and sealed under nitrogen.

Preferred formulations are those incorporating any of the preferred isothiazolones to be utilized to lower Lp(a). Especially preferred formulations are those containing an isothiazolone of Formula II.

We claim:

1. A method for lowering plasma Lp(a) levels in a mammal comprising administering an Lp(a) lowering amount of a compound of Formula I

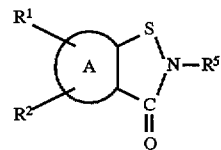

wherein:

A is a monocyclic ring having 5 or 6 ring atoms, or a bicyclic ring having from 9 to 12 ring atoms, the ring atoms being selected from carbon and optionally up to 3 heteroatoms selected from O, S, and N;

$R^1$ and $R^2$ independently are hydrogen, halo, $C_1$-$C_6$ alkyl, $C_3$-$C_6$ cycloalkyl, Het$(CR^6R^7)_m$-, phenyl-$(CR^6R^7)_m$-, O-$C_1$-$C_6$ alkyl, hydroxy, nitro, cyano, $NR^3R^4$, $NR^3COR^4$, $CO_2R^3$, $CONR^3R^4$, $S(O)_mR^3$, $SO_3H$, $S(O)_m NR^3R^4$, $COR^3$, or taken together are oxo (O=) or methylene dioxy (-O-$CH_2$-O-);

m is 0, 1, or 2;

$R^3$ and $R^4$ independently are hydrogen, $C_1$-$C_6$ alkyl, $C_3$-$C_6$ cycloalkyl, Het$(CR^6R^7)_m$-, or phenyl-$(CR^6R^7)_m$-;

$R^6$ and $R^7$ independently are hydrogen, $C_1$-$C_6$ alkyl, $CO_2R^3$, hydroxy, $CONR^3R^4$, or cyano;

$R^5$ is hydrogen, $C_1$-$C_6$ alkyl, $COC_1$-$C_6$ alkyl, $C_3$-$C_6$ cycloalkyl, phenyl-$(CR^6R^7)_m$-, Het$(CR^6R^7)_m$-; and wherein the foregoing alkyl, cycloalkyl, phenyl, and Het groups may optionally be substituted with from 1 to 3 groups selected from halo, hydroxy, nitro, $NR^3R^4$, $NR^3COR^4$, $CO_2R^3$, $CONR^3R^4$, $S(O)_mR^3$, $S(O)_m NR^3R^4$, and $COR^3$, where m, $R^3$, and $R^4$ are as defined above;

and the pharmaceutically acceptable salts and solvates thereof.

2. A method of Claim 1 employing a compound wherein A is a monocyclic ring having 6-ring atoms, one or two of which are heteroatoms selected from O, S, and N.

3. A method of Claim 2 employing a compound wherein A is a monocyclic aromatic ring.

4. A method of claim 3 employing a compound of the formula

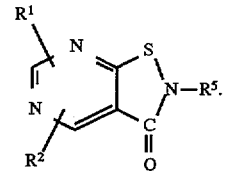

5. A method of Claim 4 employing a compound wherein $R^5$ is $C_1$-$C_6$ alkyl or substituted $C_1$-$C_6$ alkyl.

6. A method of employing a compound of the formula

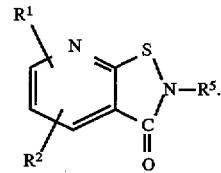

7. A method of Claim 6 employing a compound wherein $R^5$ is $C_1$-$C_6$ alkyl, substituted $C_1$-$C_6$ alkyl, or substituted or unsubstituted phenyl-$(CR^6R^7)_m$-.

8. A method of Claim 1 employing a compound of the Formula II

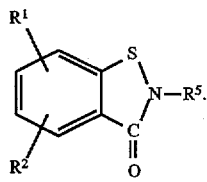

II

9. A method of Claim 8 employing a compound wherein $R^2$ is hydrogen.

10. A method of Claim 9 employing a compound wherein $R^5$ is $C_1$-$C_6$ alkyl, substituted $C_1$-$C_6$ alkyl, phenyl-$(CR^6R^7)_m$- or substituted phenyl-$(CR^6R^7)_m$-.

11. A method of claim 10 employing a compound wherein $R^5$ is

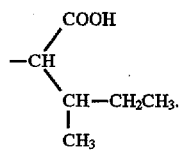

12. The method of Claim 11 employing
[S-(R*,R*)]-3-Methyl-2-(3-oxo-3H-benzo[d]isothiazol-2-yl)pentanoic acid;
2-(6-Methoxy-3-oxo-3h-benzo[d]isothiazol-2-yl)-pentanoic acid;
(S)-4-Methyl-2-(5-fluoro-3-oxo-3h-benzo[d]isothiazol-2-yl)-pentanoic acid; and
(S)-4-Methyl-2-(6-methyl-3-oxo-3h-benzo[d]isothiazol-2-yl)-pentanoic acid.

13. The method of Claim 11 employing a compound wherein $R^5$ is

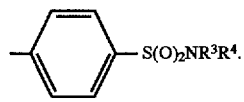

14. The method of Claim 13 employing
4-(3-Oxo-3H-benzo[d]isothiazol-2-yl) benzene sulfonamide;
N-Acetyl-4-(3-oxo-3-h-benzo[d]isothiazol-2-yl)-benzenesulfonamide;
4-(5-Methoxy-3-oxo-3h-benz[d]isothiazol-2-yl)-benzenesulfonamide;
4-(6-Methyl-3-oxo-3h-benzo[d]isothiazol-2-yl)-benzenesulfonamide;
4-(6-Fluoro-3-oxo-3h-benzo[d]isothiazol-2-yl)-benzenesulfonamide;
4-(5-Methyl-3-oxo-3h-benzo[d]isothiazol-2-yl)-benzenesulfonamide.

15. A method for treating restenosis comprising administering to an animal in need of such treatment an Lp(a) lowering amount of a compound of Formula I.

16. A method for preventing stroke comprising administering to a mammal an LID(a) lowering amount of a compound of Formula I.

17. A method for treating angina comprising administering to an animal in need of such treatment an LID(a) lowering amount of a compound of Formula I.

* * * * *